(12) United States Patent  
Rappaport et al.

(10) Patent No.: US 9,111,180 B2  
(45) Date of Patent: *Aug. 18, 2015

(54) MEDICAL IMAGE ANALYSIS

(75) Inventors: Dan Rappaport, Tel Aviv (IL); Ram Nathaniel, Tel Aviv (IL)

(73) Assignee: ORTHOPEDIC NAVIGATION LTD., Ramat Hasharon (IL)

( * ) Notice: Subject to any disclaimer, the term of this patent is extended or adjusted under 35 U.S.C. 154(b) by 321 days.

This patent is subject to a terminal disclaimer.

(21) Appl. No.: 13/334,110

(22) Filed: Dec. 22, 2011

(65) Prior Publication Data

US 2012/0183184 A1  Jul. 19, 2012

Related U.S. Application Data

(63) Continuation of application No. 11/858,947, filed on Sep. 21, 2007, now Pat. No. 8,090,166.

(60) Provisional application No. 60/826,448, filed on Sep. 21, 2006.

(51) Int. Cl.
| | |
|---|---|
| *G06K 9/00* | (2006.01) |
| *G06K 9/62* | (2006.01) |
| *A61B 5/107* | (2006.01) |
| *G06T 5/00* | (2006.01) |
| *G06T 7/00* | (2006.01) |
| *A61B 5/00* | (2006.01) |

(52) U.S. Cl.
CPC .............. *G06K 9/6255* (2013.01); *A61B 5/107* (2013.01); *G06T 5/006* (2013.01); *G06T 7/0012* (2013.01); *G06T 7/0046* (2013.01); *A61B 5/4509* (2013.01); *A61B 5/4528* (2013.01); *G06K 2209/055* (2013.01); *G06T 2207/30004* (2013.01)

(58) Field of Classification Search
USPC ......... 382/100, 128–132, 286, 173, 190, 258, 382/154, 254; 378/62, 51, 98.2, 98.6, 4; 600/105, 427, 407, 410

See application file for complete search history.

(56) References Cited

U.S. PATENT DOCUMENTS

| | | |
|---|---|---|
| 581,540 A | 4/1897 | Dennis |
| 1,396,920 A | 11/1921 | Brostrom |
| 2,819,526 A | 1/1958 | Brown, Jr. |
| 3,706,883 A | 12/1972 | McIntyre |
| 3,770,956 A | 11/1973 | Johnson |
| 3,848,136 A | 11/1974 | Seldin |

(Continued)

FOREIGN PATENT DOCUMENTS

| | | |
|---|---|---|
| EP | 0655861 A1 | 5/1995 |
| EP | 1255403 A3 | 3/2004 |

(Continued)

OTHER PUBLICATIONS

B.K.P. Horn and M.J. Brooks, "Shape from Shading" MID Press, Cambridge Mass (1989).

(Continued)

*Primary Examiner* — Hadi Akhavannik

(74) *Attorney, Agent, or Firm* — Vladimir Sherman; Professional Patent Solutions

(57) ABSTRACT

A method of analyzing a medical image, the method comprising making a measurement on a 2D medical image of an organ and correcting the measurement in view of an angle of incidence between an imaging instrument and an imaged organ in the 2D medical image.

20 Claims, 16 Drawing Sheets

Angle of Incidence: 20

(56) References Cited

U.S. PATENT DOCUMENTS

| | | | |
|---|---|---|---|
| 4,005,527 A | | 2/1977 | Wilson et al. |
| 4,736,399 A | | 4/1988 | Okazaki |
| 4,890,311 A | | 12/1989 | Saffer |
| 4,915,112 A | | 4/1990 | Singer |
| 4,918,715 A | | 4/1990 | Krupnick et al. |
| 5,052,035 A | | 9/1991 | Krupnick |
| 5,123,056 A | | 6/1992 | Wilson |
| 5,262,856 A | | 11/1993 | Lippman et al. |
| 5,285,785 A | | 2/1994 | Meyer |
| 5,400,513 A | | 3/1995 | Duffield |
| 5,409,004 A | | 4/1995 | Sloan |
| 5,551,160 A | | 9/1996 | Ferris et al. |
| 5,640,436 A | * | 6/1997 | Kawai et al. ............... 378/4 |
| 5,649,032 A | | 7/1997 | Burt et al. |
| 5,687,331 A | * | 11/1997 | Volk et al. ............... 715/840 |
| 5,801,385 A | | 9/1998 | Endo et al. |
| 5,833,607 A | | 11/1998 | Chou et al. |
| 5,841,833 A | * | 11/1998 | Mazess et al. ............... 378/98.9 |
| 5,970,119 A | | 10/1999 | Hofmann |
| 6,075,879 A | | 6/2000 | Roehrig et al. |
| 6,097,833 A | | 8/2000 | Lobregt et al. |
| 6,101,238 A | | 8/2000 | Murthy et al. |
| 6,196,715 B1 | | 3/2001 | Nambu et al. |
| 6,206,566 B1 | * | 3/2001 | Schuetz ............... 378/205 |
| 6,243,439 B1 | | 6/2001 | Arai et al. |
| 6,356,621 B1 | | 3/2002 | Furumori et al. |
| 6,396,903 B1 | | 5/2002 | Wenstrup |
| 6,618,494 B1 | | 9/2003 | Nonay et al. |
| 6,666,579 B2 | | 12/2003 | Jensen |
| 6,792,071 B2 | * | 9/2004 | Dewaele ............... 378/62 |
| 6,925,200 B2 | | 8/2005 | Wood et al. |
| 6,990,229 B2 | | 1/2006 | Ohishi |
| 7,015,906 B2 | | 3/2006 | Olschewski et al. |
| 7,396,161 B2 | | 7/2008 | Schmitt |
| 7,453,977 B2 | * | 11/2008 | DiBianca et al. ............... 378/19 |
| 7,499,579 B2 | | 3/2009 | Squilla et al. |
| 7,611,466 B2 | * | 11/2009 | Chalana et al. ............... 600/443 |
| 7,664,298 B2 | * | 2/2010 | Lang et al. ............... 382/128 |
| 7,702,380 B1 | | 4/2010 | Dean |
| 7,773,829 B1 | | 8/2010 | Brandt |
| 7,797,030 B2 | | 9/2010 | Lahm et al. |
| 7,871,406 B2 | | 1/2011 | Nields et al. |
| 7,877,128 B2 | | 1/2011 | Schwartz |
| 7,905,924 B2 | | 3/2011 | White |
| 7,995,822 B2 | * | 8/2011 | Lang et al. ............... 382/128 |
| 8,090,166 B2 | * | 1/2012 | Rappaport et al. ............ 382/128 |
| 8,104,958 B2 | | 1/2012 | Weiser et al. |
| RE43,282 E | * | 3/2012 | Alexander et al. ............ 600/427 |
| 8,463,006 B2 | * | 6/2013 | Prokoski ............... 382/128 |
| 8,611,697 B2 | | 12/2013 | Nathaniel et al. |
| 8,855,390 B2 | | 10/2014 | Bismuth et al. |
| 2003/0014034 A1 | | 1/2003 | Strobel |
| 2004/0034298 A1 | | 2/2004 | Johnson et al. |
| 2004/0086082 A1 | | 5/2004 | Foos et al. |
| 2004/0111024 A1 | | 6/2004 | Zheng et al. |
| 2005/0104018 A1 | | 5/2005 | Chang et al. |
| 2005/0213849 A1 | | 9/2005 | Kreang-Arekul et al. |
| 2006/0120583 A1 | * | 6/2006 | Dewaele ............... 382/128 |
| 2006/0154198 A1 | | 7/2006 | Durbin et al. |
| 2006/0177150 A1 | | 8/2006 | Uyttendaele et al. |
| 2007/0041508 A1 | | 2/2007 | Tubbs |
| 2008/0056547 A1 | | 3/2008 | Kokubun et al. |
| 2008/0111831 A1 | | 5/2008 | Son et al. |
| 2008/0118023 A1 | | 5/2008 | Besson |
| 2008/0242971 A1 | | 10/2008 | Klingenbeck-Regn |
| 2009/0221908 A1 | | 9/2009 | Glossop |
| 2009/0310845 A1 | | 12/2009 | Ogawa et al. |
| 2010/0135467 A1 | | 6/2010 | King et al. |
| 2010/0232670 A1 | * | 9/2010 | Blanchard et al. ............ 382/132 |
| 2011/0019884 A1 | | 1/2011 | Blau |
| 2011/0102461 A1 | | 5/2011 | Schultz et al. |
| 2011/0188726 A1 | | 8/2011 | Nathaniel et al. |
| 2012/0059248 A1 | | 3/2012 | Holsing et al. |
| 2013/0211244 A1 | | 8/2013 | Nathaniel |
| 2013/0322726 A1 | | 12/2013 | Nathaniel |

FOREIGN PATENT DOCUMENTS

| | | |
|---|---|---|
| EP | 1498849 A2 | 1/2005 |
| EP | 1632181 B1 | 11/2007 |
| WO | WO2009022266 A1 | 2/2009 |
| WO | WO2011042832 A1 | 4/2011 |

OTHER PUBLICATIONS

Harris, J.H., "The normal cervical spine" (1987). (Web-link: http://rapidshare.com/files/213791249/TheNormalCervicalSpine.pdf.html).

Segonne, Florent, "Segmentation of Medical Images underTopological Constraints", 2005, USA.

Maintz, et al.; "A Survey of Medical Image Registration"; 1998; pp. 1-37; pp. 1-3, 7-142; The Netherlands.

Russakoff, et al., "Fast Intensity-based 2D-3D Image Registration of Clinical Data Using Light Fields", 2003, pp. 1-7, USA.

Chen, et al., "Automatic Extraction of Femur Contours from Hip X-ray Images", 2005, pp. 1-10, Singapore.

Kass, et al., "Snakes: Active Contour Models", 1988, pp. 321-331, The Netherlands.

Long, et al., "Segmentation and feature extraction of cervical spine x-ray images", 1999, pp. 1037-1046, USA.

Zitova, et al., "Image registration methods: a survey", 2003, pp. 977-1000, Czech Republic.

Lee, et al., "Image Morphing Using Deformation Techniques", 1996, pp. 3-23, Korea.

Parkinson, et al., "Methodological principles for factual analysis of trabecular bone", 2000, pp. 134-142, Australia.

Geraets, et al., "The Radiographic Trabecular Pattern of Hips in Patients With Hip Fractures and in Elderly Control Subjects", 1998, pp. 165-173, The Netherlands.

Geraets, et al., "Analysis of the radiographic trabecular pattern", 1991, pp. 575-581, The Netherlands.

Dougherty, et al., "Lacunarity analysis of spatial pattern in CT images of vertebral trabecular bone for assessing osteoporosis", 2002, pp. 129-138, Kuwait.

Behiels, et al, "Evaluation of image features and search strategies for segmentation of bone structures in radiographs using Active Shape Models", 2002, pp. 47-62, Belgium.

Lum, et al., "Cominging Classifiers for Bone Fracture Detection in X-ray Images", 2005, pp. 1149-1152, Singapore.

Cocosco, et al., "BrainWeb: Online Interface to a 3D MRI Simulated Brain Database", 1997, S425-27, Canada.

Maintz, et al.; "An Overview of Medical Image Registration Methods"; 1998; pp. 1-22; The Netherlands.

Joskowicz L et al: "Long Bone Panoramas From Fluoroscopic X-Ray Images", IEEE Transactions on Medical Imaging, IEEE Service Center, Piscataway, NJ, US, vol. 23, No. 1, Jan. 1, 2004, pp. 26-35, XP011104510, ISSN: 0278-0062, DOI: DOI:10.1109/TMI.2003.819931.

Peter Messmer et al: "Image Fusion for Intraoperative Control of Axis in Long Bone Fracture Treatment", European Journal of Trauma, Urban & Vogel, MU, vol. 32, No. 6, Dec. 1, 2006, pp. 555-561, XP019462173, ISSN: 1615-3146, DOI: DOI:10.1007/S00068-006-5159-5.

* cited by examiner

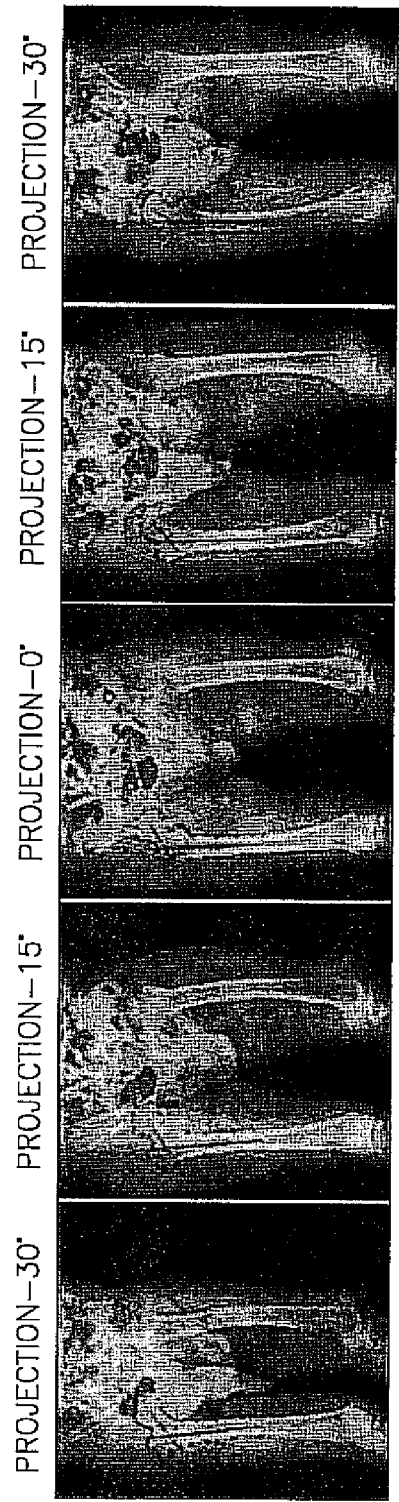
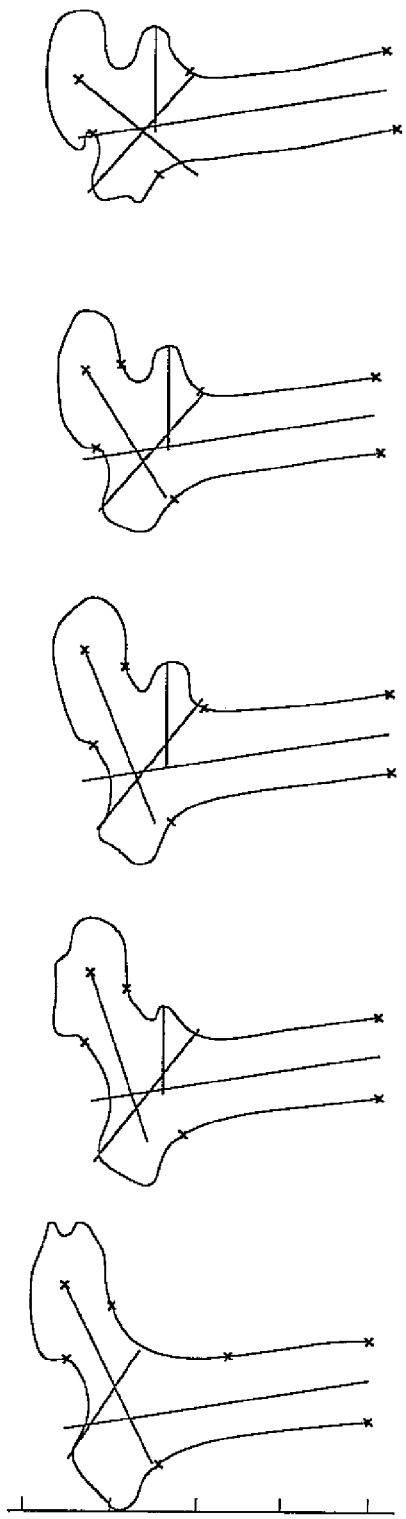
FIG.5A  FIG.5B  FIG.5C  FIG.5D  FIG.5E

 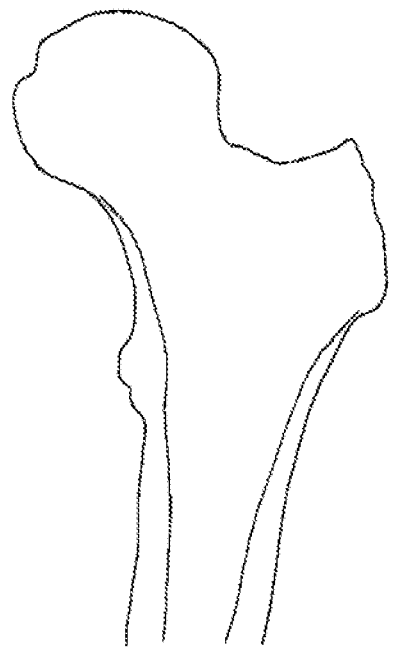
FIG.6A  FIG.6B
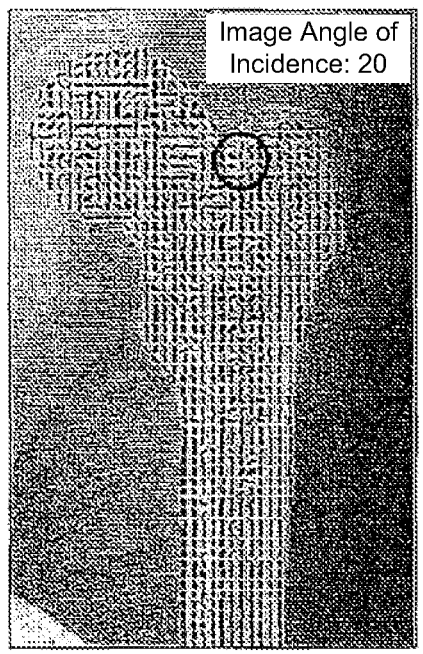 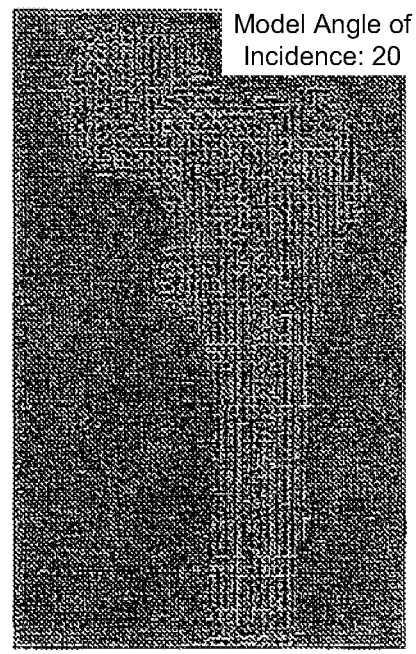
FIG.7A  FIG.7B

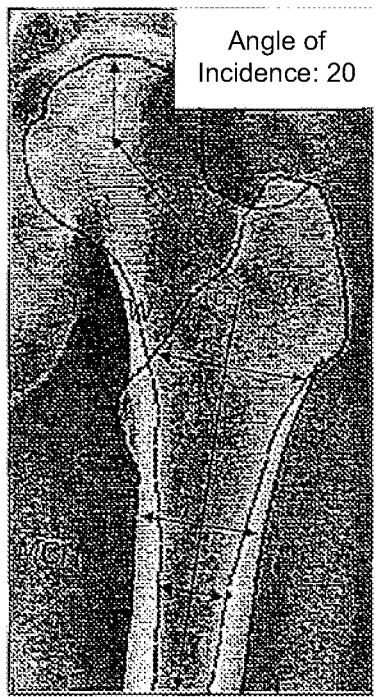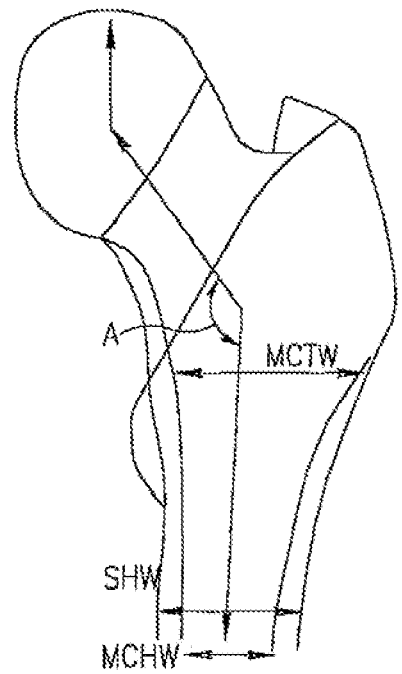
FIG.8A  FIG.8B
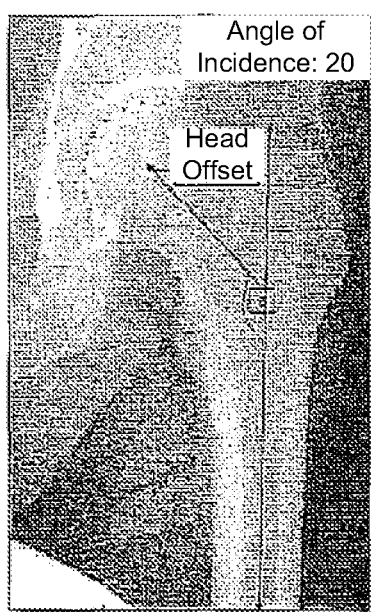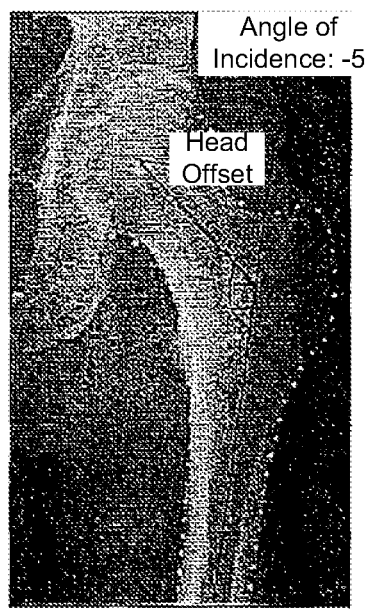
FIG.9A  FIG.9B

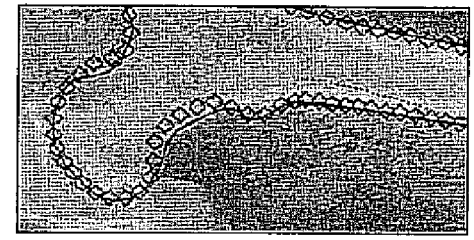
FIG.12E MODEL 5- ANGLE-30 GRADE 0.9
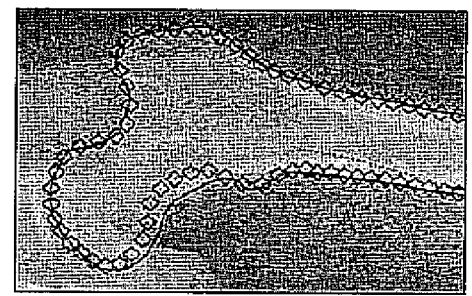
FIG.12D MODEL 4- ANGLE-15 GRADE 0.93
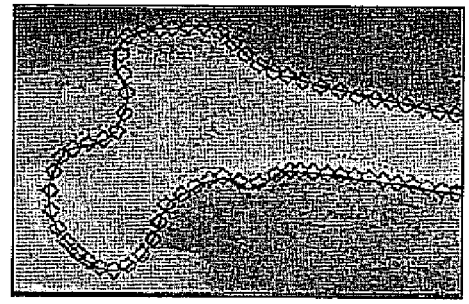
FIG.12C MODEL 3- ANGLE-0 GRADE 0.99
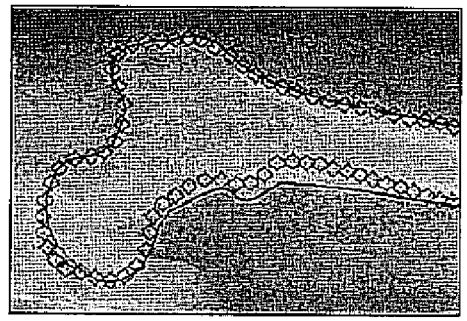
FIG.12B MODEL 2- ANGLE-15 GRADE 0.82
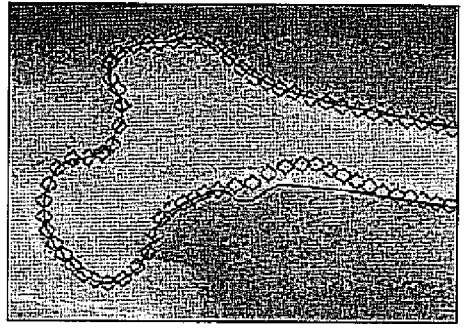
FIG.12A MODEL 1- ANGLE-30 GRADE 0.79

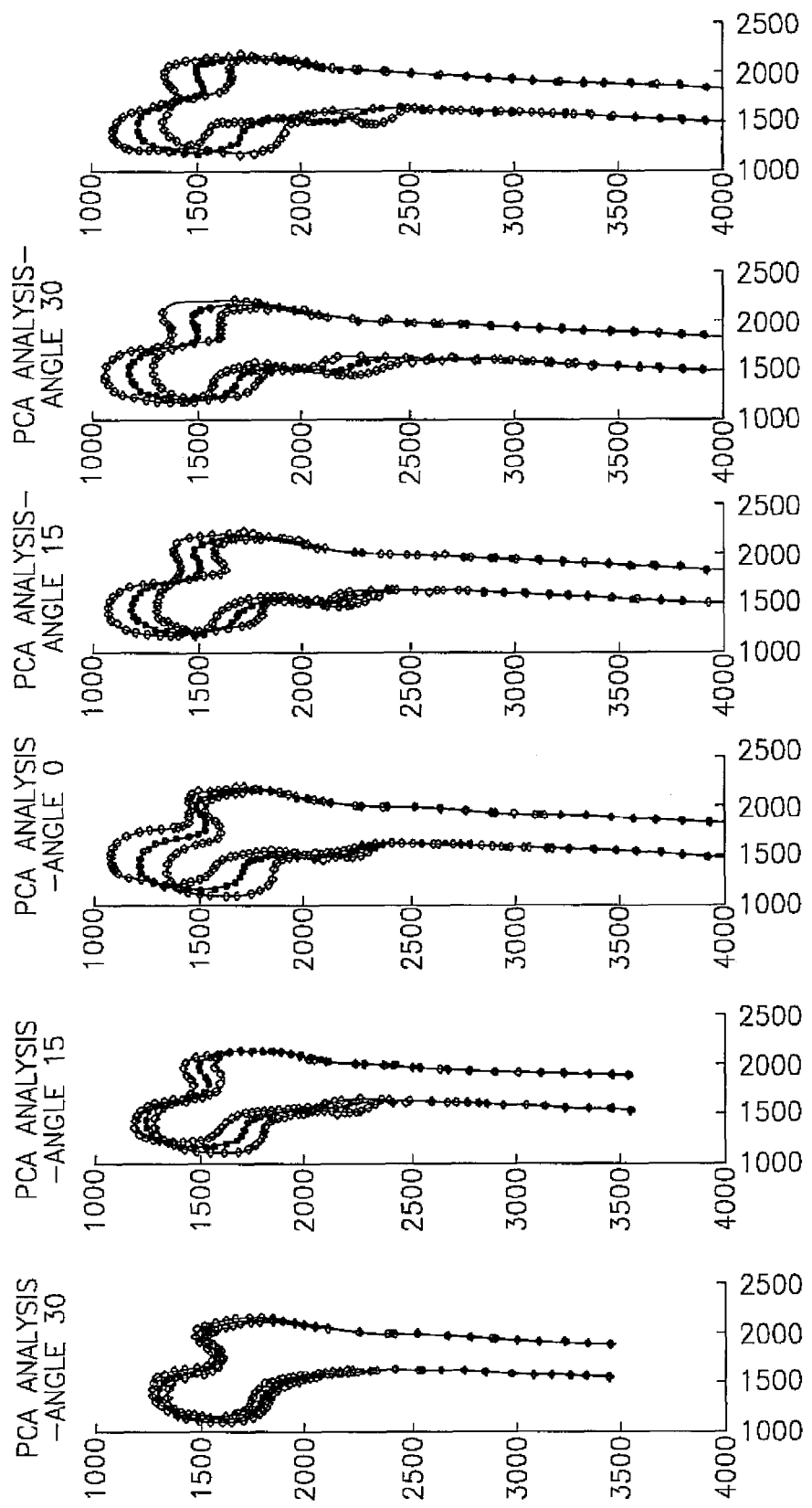

PLANE JOINT

HINGE JOINT

PIVOT JOINT

CONDYLOID JOINT

SADDLE JOINT

BALL-AND-SOCKET JOINT

SWING

SPIN

MEDICAL IMAGE ANALYSIS

RELATED APPLICATIONS

The present application is a Continuation Application of U.S. patent application Ser. No. 11/858,947, filed on Sep. 21$^{st}$, 2007 now U.S. Pat. No. 8,090,166, which '947 application claims the benefit of U.S. Provisional Patent Application Ser. No. 60/826,448 filed on Sep. 21$^{st}$, 2006. Each of the aforementioned applications is hereby incorporated into this application by reference in its entirety.

FIELD OF THE INVENTION

The present invention relates to systems and methods for analysis of medical images.

BACKGROUND OF THE INVENTION

Many algorithms for automated analysis of medical images, such as X-ray images, have been suggested. In general, the automated analyses rely upon segmentation and/or comparison to a model. These automated analyses have been applied to analyses of bone mineral density, fractures and lesions. However, previously available automated analyses can be influenced by distortion caused by an angle of incidence of X-ray beams with respect to an imaged bone. FIGS. 9A and 9B show that a change in the angle of incidence from −10 degrees (FIG. 9A) to +30 degrees (FIG. 9B) can cause significant changes in important measured anatomic features. For example, the femur head offset (indicated by the arrow) is 5.2 cm at −10 degrees and 2.1 cm at +30 degrees. The head shaft angles (θ) are 135° and 153°, respectively. As a result, even when automated image analyses accurately measure selected image parameters, the automatically measured parameters may be difficult to evaluate.

Manual analysis by a radiologist is subject to similar influence from angle of incidence, although to a lesser degree. An expert radiologist may be able to judge an approximate angle of incidence for a particular image and mentally correct measurements. However, it may take many years of clinical experience to acquire this level of experience. Also, a radiologist with vast experience in evaluating hip X-rays may have significantly less experience with images of other body portions (e.g ankle or spine). Alternatively or additionally, an "eyeball" correction tends to be more qualitative than quantitative.

It is known to register a 3D image (e.g. CT scan) of an organ from a specific patient onto a 2D image acquired from the same patient (e.g., an X-ray image). This permits information from CT images to be used during interventional procedures by registering the CT scan to an intra-operative X-ray fluoroscopy image. This method registers a fluoroscopy image with respect to a CT scan ("An Overview of Medical Image Registration Models" Maintz, J. B. A., & Viergever, M. A. (1998) *An Overview of Medical Image Registration Methods*. UU-CS (Ext rep. 1998-22, Utrecht University Information and Computing Sciences, Utrecht, the Netherlands) and also "Fast Intensity-based 2D-3D Image Registration of Clinical Data Using Light Fields" (2003) Daniel B. Russakoff, Torsten Rohlfing, Calvin Maurer; the contents of which are each fully incorporated herein by reference). Methods described in these references employ a 3D scan from a subject to evaluate a 2D image from the same subject and do not consider determining an angle of incidence of a 2D image without acquiring a 3D scan from the same patient.

Automatic contour and/or segmentation analysis of medical images are generally known in the art.

Chen et al. describe a contour analysis model which relies upon an algorithm based upon a plurality of 2D images with manually defined Femur contours to determine Femur contours in additional input images. (Ying Chen et al. (2005) "Automatic Extraction of Femur Contours from Hip X-Ray Images", CVBIA. 2005: 200-209; the contents of which are fully incorporated herein by reference).

Exemplary segmentation models are described by Kass et al. and by Long and Thoma (M. Kass et al. (1987) "Snakes: Active contour models". In First International Conference on Computer Vision; London; pages 259-268; L. R. Long and G. R. Thoma (1999) "Segmentation and feature extraction of cervical spine X-ray images" Proc. SPIE Medical Imaging: Image Processing, San Diego, Calif., 3661:1037-1046 the contents of which are each fully incorporated herein by reference).

Registration of one image with respect to another has been attempted by a variety of methods. This subject is reviewed in "Image registration methods: a survey", by Barbara Zitova and Jan Flusser (Image and Vision Computing 21 (2003) 977-1000). The contents of this article are fully incorporated herein by reference.

U.S. Pat. No. 6,990,229 describes a system for alignment and simultaneous display of 2 or more 3D medical images. The disclosure of this patent is fully incorporated herein by reference.

U.S. Pat. No. 6,075,879 describes systems and methods for computer aided detection of suspicious lesions, primarily in breast tissue. This patent describes comparison of two 2D images acquired from different known angles. The disclosure of this patent is fully incorporated herein by reference.

Horn and Brooks describe reconstruction of the shape of a smooth object from a given single gray level image (B. K. P. Horn and M. J. Brooks (1989) "Shape from Shading" MIT Press, Cambridge Mass). According to Horn and Brooks, the shading of an object is a function of the projection of the surface normal onto the light source direction. However, shape from shading methods as described by Horn are useful primarily for images acquired with light, which is reflected. The contents of this article are fully incorporated herein by reference.

U.S. Pat. No. 6,206,566 discloses a system for determining the angle of incident X-ray beams using X-ray positive marks deployed during image acquisition. All methods described in this patent must be implemented during image capture. The disclosure of this patent is fully incorporated herein by reference.

SUMMARY OF THE INVENTION

A broad aspect of some embodiments of the invention relates to improving interpretation of medical images by estimating an angle of incidence between an imaging instrument and an imaged organ when performing an image analysis.

A broad aspect of some embodiments of the invention relates to a spatial model of an organ in three dimensions based upon 2D medical images from a plurality of subjects. In an exemplary embodiment of the invention, the 2D medical images are X-ray images.

An aspect of some embodiments of the invention relates to estimating an angle of incidence of a conventional X-ray image after capture of the image. Optionally, estimation of the angle of incidence improves an automated analysis of the image. In an exemplary embodiment of the invention, the conventional X-ray image is input into a system which compares the input image to a series of angle specific 2D models based upon previously acquired 2D images from many subjects. Optionally, the previously acquired 2D images include X-ray images and/or 2D images extracted from tomographic scans.

Optionally, exemplary embodiments of the invention are able to estimate the angle of incidence of an input image without performing a complete segmentation. In an exemplary embodiment of the invention, estimation of angle of incidence before completion of segmentation relies upon matching of reference points.

Optionally, the reference points are used to define a contour, for example by segmentation. In an exemplary embodiment of the invention, angle of incidence is estimated by analyzing the contour with respect to contours of the 2D models.

Optionally, approximation of angle of incidence includes interpolation. In an exemplary embodiment of the invention, each angle specific 2D model is a statistical model comprising an average representation and a statistical variance. The statistical models define one or more determinants selected from contours (C), inner bone parameters (P) and anatomic features (F) as average values bracketed by an indication of variance (e.g. standard deviation or standard error of the mean). Optionally, two or more of different types of determinants are linked in a single model. For bones, C is generally a primary determinant of the model.

An aspect of some embodiments of the invention relates to constructing a model, optionally a statistical model, based upon previously acquired images from many subjects, each image with a known angle of incidence. In an exemplary embodiment of the invention, the model comprises a series of 2D models, each 2D model characterized by an angle of incidence.

Optionally, the previously acquired images are standard X-ray images or are extracted from 3D images (e.g. computerized tomography scans). In some exemplary embodiments of the invention, a single image is divided into several organ specific images for preparation of angle specific 2D models (e.g. a single pelvic X-ray might be used for modeling of right femur, left femur and pelvic bones). In other exemplary embodiments of the invention, images of individual organs are employed to prepare angle specific 2D models (e.g. a series of lower mandible X-rays).

Optionally, the previously acquired images are acquired from subjects including actual patients and/or living volunteers and/or cadavers.

Optionally, each subject may provide one or a plurality of images, each image acquired from a known angle of incidence. Angles of incidence may be determined, for example, by direct measurement or by use of fiducial markers.

In an exemplary embodiment of the invention, angles of incidence of previously acquired images are grouped by ranges and an angle of incidence is considered "known" if it can be placed in one of the ranges. In an exemplary embodiment of the invention, ranges are defined based on one or more of a desired total number of models, analysis of actual angles of incidence in acquired images and analysis of differences between experimental model countours.

In an exemplary embodiment of the invention, a range of angles of incidence covered by a spatial model of a specific organ (e.g. femur) in a specific type of x-ray image (e.g. front or side view) is defined according to physiologic parameters of the organ and/or an expected range of error in positioning an image acquisition device with respect to the organ.

Optionally, selection of specific ranges for each individual model may be based on statistical methods and/or a rule (e.g. at least 5 models and/or no more than 8 models). For a given number of images available for model building, there is often a trade-off between increasing the number of models and decreasing the number of images used to construct each model.

Optionally, reducing a number of images used to construct a model increases variance within the model. In an exemplary embodiment of the invention, an acceptable degree of variance for a model is selected and the available images are divided into models so that none of the models exceed the acceptable level of variance.

In an exemplary embodiment of the invention, a set of images with known angles of incidence are divided to form a series of 2D models which are statistically differentiable from one another. Optionally, an iterative process is employed to achieve the desired division. In an exemplary embodiment of the invention, the iterative process produces a series of angle specific 2D models with different angular differences between different pairs of models.

In an exemplary embodiment of the invention, an angle of incidence is determined and/or recorded during capture of images used to construct the angle specific 2D models.

In an exemplary embodiment of the invention, the previously acquired 2D images from many subjects used to construct the 2D models are registered prior to determination of a normal contour. In an exemplary embodiment of the invention, registration includes scaling and/or translation and/or rotation.

In an exemplary embodiment of the invention, each angle specific 2D model of each organ is based upon 20, optionally 100, optionally 1000, optionally 10,0000, optionally 100,000 or lesser or greater or intermediate numbers of images. The number of images employed in constructing a model contributes to the statistical variation of the model. Optionally, as the number of images employed to construct a model increases, variation of the model decreases.

In an exemplary embodiment of the invention, pathologiocal images are excluded from a normal model. Optionally, one or more separate pathological models are generated. Optionally, the separation of pathological images is used to prevent outliers form unduly influencing the normal model.

In an exemplary embodiment of the invention, there is provided a method of analyzing a medical image, the method comprising:

(a) making a measurement on a 2D medical image of an organ; and
(b) correcting the measurement in view of an angle of incidence between an imaging instrument and an imaged organ in the 2D medical image.

Optionally, the method comprises:
(c) estimating the angle of incidence after acquisition of the image using reference points in the 2D medical image and without use of fiducial markers in the 2D medical image.

Optionally, the organ includes at least one bone.
Optionally, the organ includes at least one joint.
Optionally, the medical image is an X-ray image.
Optionally, the measurement includes a contour.

In an exemplary embodiment of the invention, there is provided a method of organ modeling, the method comprising:

(a) acquiring a plurality of 2D images of an organ from a plurality of subjects, each image characterized by an angle of incidence; and
(b) producing a series of angle specific 2D models, each angle specific 2D model comprising a representation of the organ based upon 2D images with angles of incidence in a defined range.

Optionally, each of the angle specific 2D models includes a group of reference points on a contour (C).

Optionally, each of the angle specific 2D models includes at least a portion of a contour (C).

Optionally, each of the angle specific 2D models includes substantially all of the contour (C).

Optionally, each of the angle specific 2D models includes at least one anatomic feature (F).

Optionally, each of the angle specific 2D models includes at least one inner Parameter (P).

Optionally, each of the angle specific 2D models includes a graphic representation of at least a portion of the organ.

Optionally, each of the angle specific 2D models includes a numerical representation of at least a portion of the organ.

Optionally, in the numerical representations of the angle specific 2D models are provided as a lookup table.

Optionally, the representation is an average representation.

Optionally, the series of angle specific 2D models comprise a spatial model of the organ.

Optionally, the angles of incidence cover a range of +90 degrees to −90 degrees.

Optionally, the angles of incidence cover a range of +60 degrees to −60 degrees.

Optionally, the angles of incidence cover a range of +45 degrees to −45 degrees.

Optionally, the angles of incidence cover a range of +30 degrees to −30 degrees.

Optionally, the angles of incidence cover a range of +10 degrees to −10 degrees.

Optionally, the plurality of 2D images of an organ are in a same view

Optionally, the plurality of 2D images of an organ are X-ray images.

Optionally, some subjects provide at least two images of the organ, each image acquired from a different angle of incidence.

Optionally, at least two of the images acquired from different angles of incidence are employed to construct a single angle specific 2D model.

Optionally, some subjects provide only a single image of the organ.

Optionally, the method comprises measurement of the angle of incidence during the acquiring.

Optionally, the methods comprise using fiducial markers during image acquisition.

Optionally, the average representation includes an indication of variance.

In an exemplary embodiment of the invention, there is provided a method of estimating an angle of incidence from which a 2D medical image was captured; the method comprising:
(a) acquiring a 2D medical image of an organ from a subject;
(b) comparing the acquired image to at least one angle specific 2D model of the organ;
(c) determining a match score between the image and the angle specific 2D model; and
(d) estimating an angle of incidence to the image based upon the match score.

Optionally, the method is applied to at least two separate 2D medical images of an organ and comprises:
(e) additionally comparing the at least two separate 2D medical images with one another while considering the estimated angle of incidence of each image.

Optionally, the method is applied to images of two contralateral organs from a same subject and comprises:
(e) additionally comparing the contralateral organs with one another while considering the estimated angle of incidence of each organ.

Optionally, the at least two separate 2D medical images each include a same organ from a same subject;
wherein the 2D medical images are acquired at different times.

Optionally, a series of angle specific 2D models are employed.

Optionally, assigning includes interpolation to an angle between two angles of the series of angle specific 2D models.

Optionally, the medical image is an X-ray image.

Optionally, the angle specific 2D models are statistical models which include an indication of variance.

Optionally, the statistical models describe at least one inner bone parameter (P) of a bone.

Optionally, the statistical models describe at least a portion of a contour (C) of a bone.

Optionally, the statistical models describe at least one anatomic feature (F) of a bone.

Optionally, the statistical models describe a joint.

Optionally, the angle specific 2D models cover angular translations in at least two planes.

Optionally, the angle specific 2D models cover angular translations of two bones comprising the joint.

In an exemplary embodiment of the invention, there is provided an image analysis system, the system comprising:
(a) an input module adapted to receive an input image of an organ;
(b) a memory containing a plurality of angle specific 2D organ models, each model characterized by an angle of incidence; and
(c) analytic circuitry adapted to estimate an angle of incidence of the input image by comparing the input image to the plurality.

Optionally, the input module comprises an image capture device.

Optionally, the analytic circuitry is adapted to determine at least one discrepancy (D) between the input image and a selected angle specific 2D organ model.

Optionally, D suggests a pathologic condition

Optionally, the system comprises a reporting module adapted to generate a report.

Optionally, the report describes at least one discrepancy (D) of at least one inner bone parameter (P) of a bone ($D_P$).

Optionally, the report describes at least one discrepancy (D) of at least a portion of a contour (C) of a bone ($D_C$).

Optionally, the report describes at least one discrepancy (D) of at least one anatomic feature (F) of a bone ($D_F$).

Optionally, the report describes at least one inner bone parameter (P) of a bone.

Optionally, the report describes at least a portion of a contour (C) of a bone.

Optionally, the report describes at least one anatomic feature (F) of a bone.

BRIEF DESCRIPTION OF THE DRAWINGS

Exemplary non-limiting embodiments of the invention described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIGS. 5A, 5B, 5C, 5D and 5E illustrate X-ray images of the hips of a single subject and corresponding diagrams of the right femur contour and parameters for angles of incidence from −30 degrees to +30 degrees in 15 degree steps;

FIG. 6A indicates contour discrepancies (black and white ring) with respect to a statistical contour model according to an exemplary embodiment of the invention for an angle of incidence of 20 degrees;

FIG. 6B illustrates a statistical contour model for an angle of incidence of 20 degrees according to an exemplary embodiment of the invention;

FIG. 7A indicates textural parameter discrepancies (black ring) with respect to a statistical parameter map for an angle of incidence of 20 degrees;

FIG. 7B illustrates a statistical textural parameter map for an angle of incidence of 20 degrees according to an exemplary embodiment of the invention;

FIG. 8A indicates anatomic feature discrepancies with respect to a statistical feature map for an angle of incidence of 20 degrees;

FIG. 8B illustrates a statistical anatomic feature map for an angle of incidence of 20 degrees according to an exemplary embodiment of the invention;

FIGS. 9A and 9B illustrate X-ray images of a femur acquired from the same patient at angles of incidence +20 degrees and −5 degrees respectively;

FIGS. 12A, 12B, 12C, 12D and 12E illustrate matching between contour models and estimated contours and determination of a best match score according to an exemplary embodiment of the invention;

FIGS. 13A, 13B, 13C, 13D, and 13E indicate Principle Component

Figure 14B:
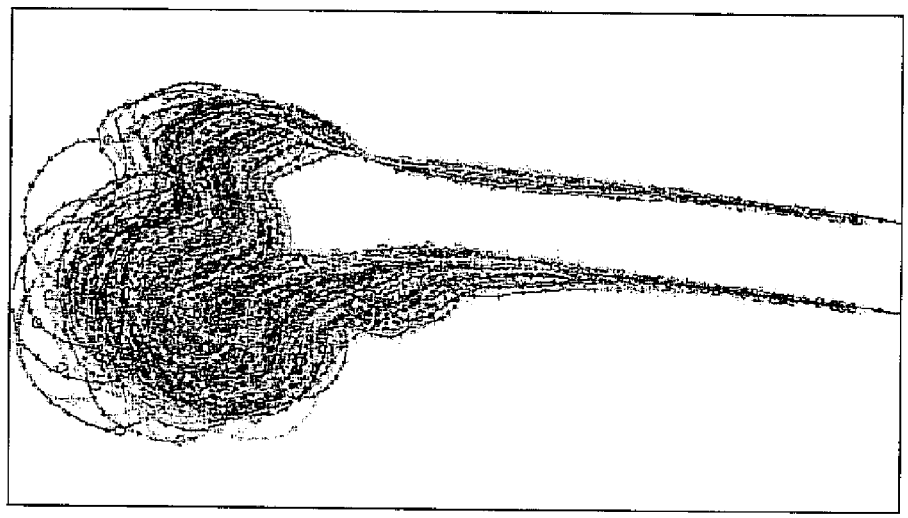
Figure 14A:
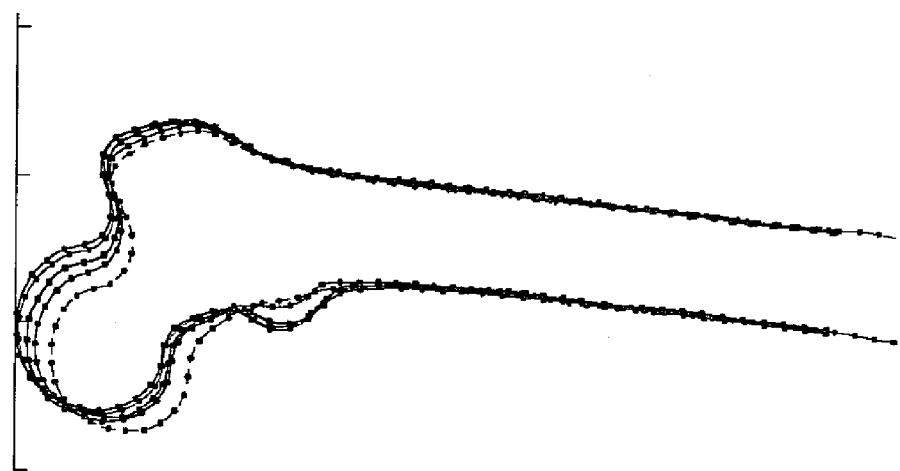

Analysis (PCA) of aligned contours comprising different angle specific 2D models (13A, 13B, 13C, 13D, and 13E correspond to models of angles of incidents in the range [−7, 7] around angles −30, −15, 0, 15, 30, respectively; Center line is the mean model contour and both external lines are one standard deviation unit according to the PCA analysis);

FIG. 13F indicates a PCA of contours from all images used in constructing the models of FIGS. 13A, 13B, 13C, 13D, and 13E; and FIG. 14A shows the 5 angle specific 2D models of Figs. FIGS. 13A, 13B, 13C, 13D, and 13E aligned with respect to one another;

FIG. 14B shows the 299 individual contours the images used in constructing the models of FIGS. 13A, 13B, 13C, 13D, and 13E.

Figure 15:
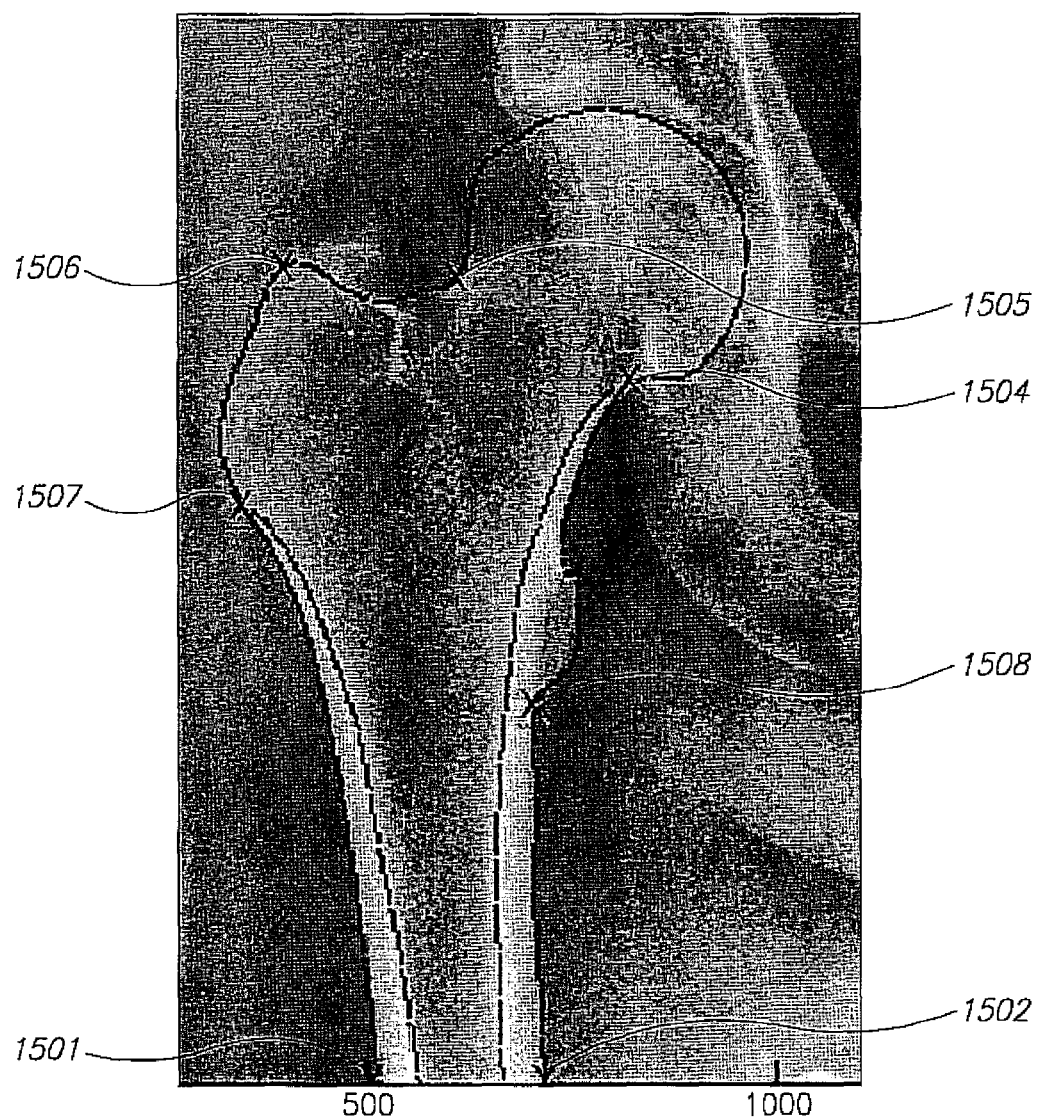
Figure 16A:
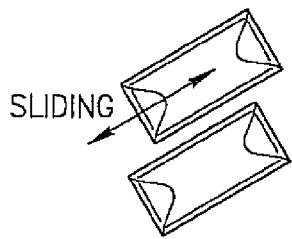
Figure 16B:
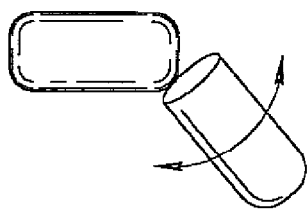
Figure 16C:
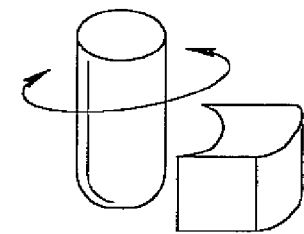
Figure 16D:
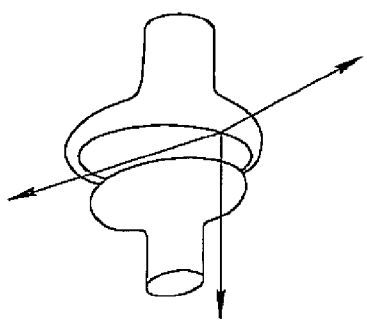
Figure 16E:
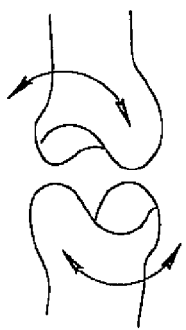
Figure 16F:
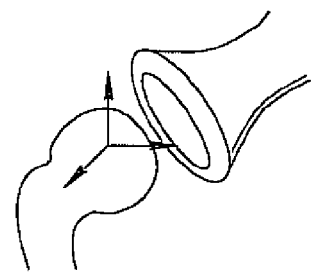
Figure 16G:
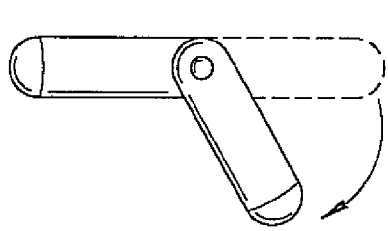
Figure 16H:
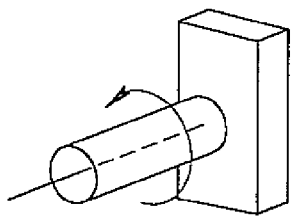

FIG. 15 depicts manually selected reference points on a contour superimposed on. an X-ray image;

FIGS. 16A, 16B, 16C, 16D, 16E and 16F are simplified schematic representations of common joint types (diarthrosis): and FIGS. 16G and 16H illustrate swing and spin movement within a joint respectively.

DETAILED DESCRIPTION OF EXEMPLARY EMBODIMENTS

Overview

Figure 1A:
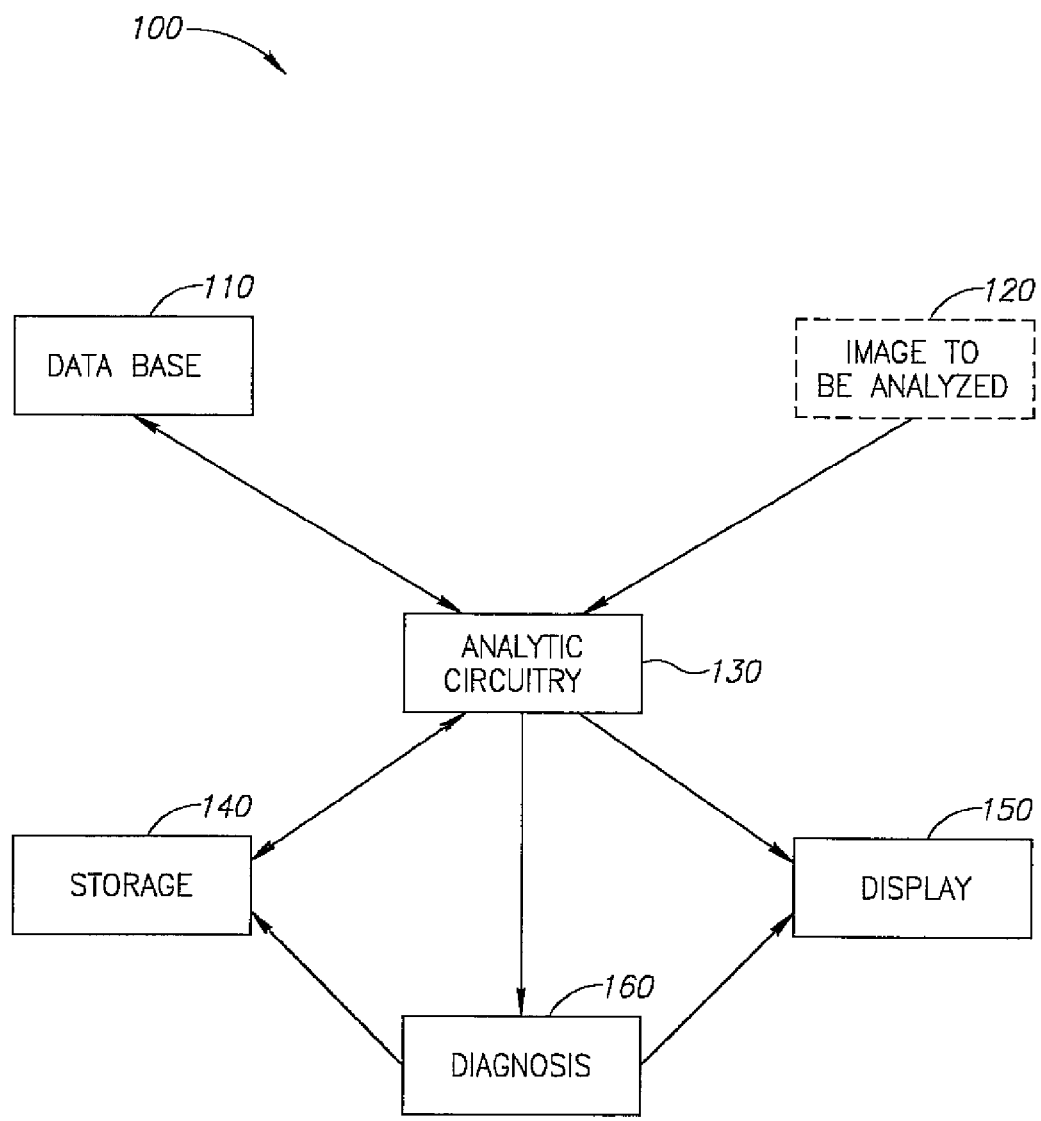
FIG. 1A is a schematic representation of an exemplary image analysis system according to some embodiments of the invention.

FIG. 1A is a schematic representation of an exemplary medical image analysis system 100 according to some embodiments of the invention. System 100, or components thereof, can be installed on a network (e.g. LAN or Internet). Arrows represent communication via any available channel of communication.

Figure 1B:
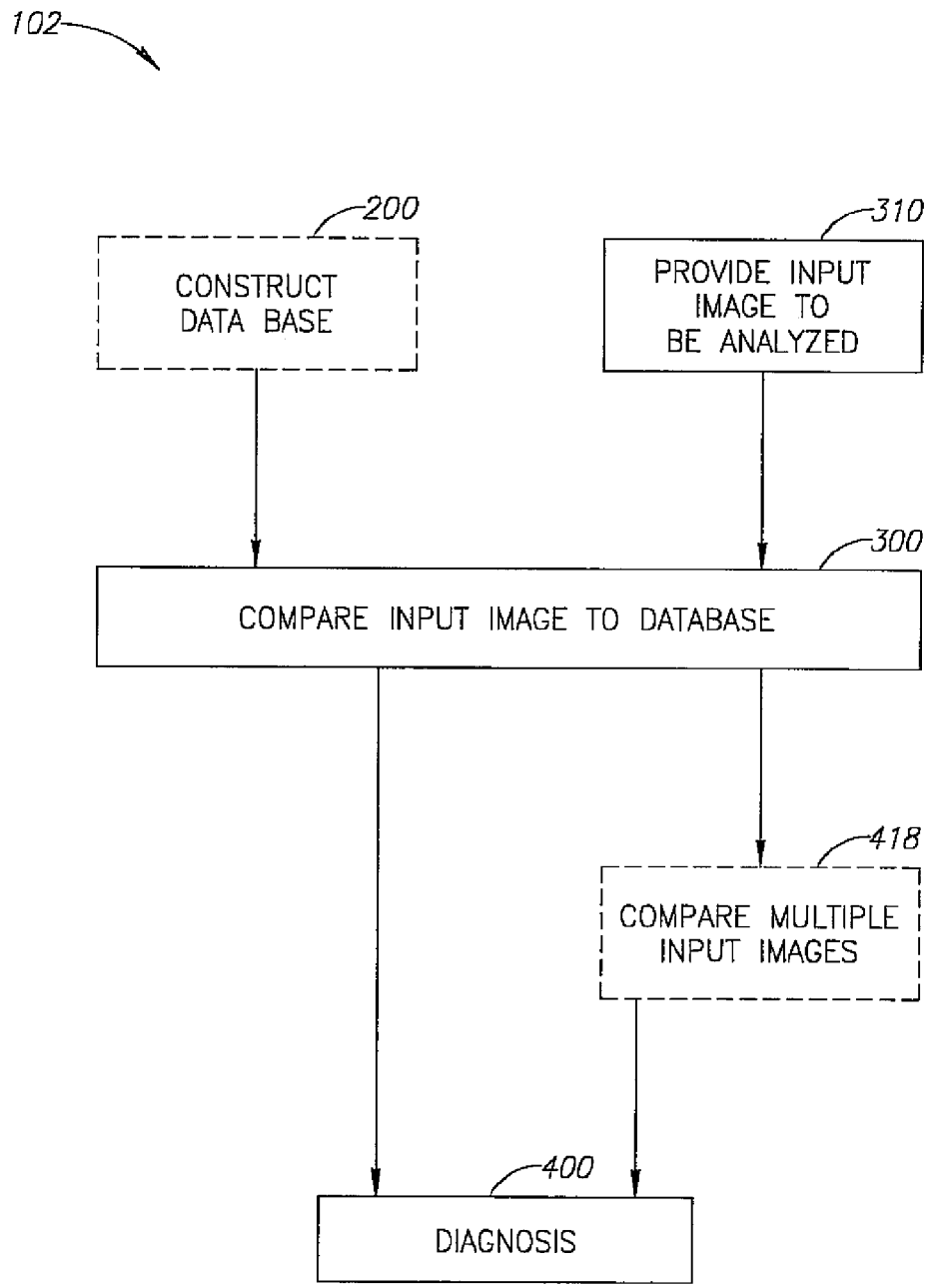
FIG. 1B is a simplified flow diagram illustrating the progression from input image to diagnosis according to exemplary embodiments of the invention.

FIG. 1B illustrates in general terms a method 102 for image analysis which relies upon angle specific 2D models. In an exemplary embodiment of the invention, angle specific 2D models contribute to increased accuracy and/or reliability of the image analysis. The following description refers to both FIGS. 1A and 1B.

Various actions indicated in FIG. 1B are depicted in greater detail in FIGS. 2A, 2B, 3A, 3B and 4 and described below.

For example, method 102 indicates only that a database 110 has been previously constructed 200 when input image 120 is provided 310. Details of an exemplary method of database construction 200 are presented in FIGS. 2A and 2B and described hereinbelow. Optionally, database 110 is updated over time.

Details of an exemplary method of comparison 300 are presented in FIGS. 3A and 3B and described hereinbelow.

Exemplary diagnostic methods 400, are presented in FIG. 4 and described hereinbelow.

System 100 (FIG. 1A) comprises a database 110. According to various exemplary embodiments of the invention, database 110 can include at least one angle specific 2D model, optionally a statistical model, of at least one organ and/or a plurality of individual images of the at least one organ. In an exemplary embodiment of the invention, the images are X-ray images and the organs are bones.

In a first set of exemplary embodiments of the invention, individual images of the organ (as opposed to prepared angle specific 2D models) are stored in database 110. According to these embodiments of the invention, when input image 120 is provided 310, analytic circuitry 130 generates a series of angle specific 2D models "on the fly" in response to receipt of image to be analyzed 120. "On the fly" exemplary embodiments offer a possibility of ongoing updates to the models by adding additional images to the database, but impose an increased computing burden on analytic circuitry 130.

In a second set of exemplary embodiments of the invention, a series of "ready to use" 2D models of the organ, each model characterized by an angle of incidence θ, is stored in database 110. Optionally, individual images used to construct the models are also retained in database 110 or in a separate storage. "Ready to use 2D models" exemplary embodiments are less flexible than the "on the fly" embodiments in terms of model updates, but impose a reduced computing burden on analytic circuitry 130.

In an exemplary embodiment of the invention, the series of angle specific 2D models constitute a partial spatial model in 3 dimensions.

FIG. 1B shows that provision 310 of an image to be analyzed 120 is followed by comparison 300 of image 120 to database 110 by analytic circuitry 130. Optionally, comparison 300 can be to models residing in database 110 or to models constructed "on the fly" from images residing in database 110. In an exemplary embodiment of the invention, comparison 300 estimates an angle of incidence θ of input image 120 by identifying one of the of angle specific 2D models as a best fit to input image 120.

In an exemplary embodiment of the invention, analytic circuitry 130 is adapted to receive the image 120 to be analyzed. In some exemplary embodiments of the invention, receipt of image 120 is directly from a digital X-ray camera (not pictured) connected to analytic circuitry 130, for example by an interface cable or across a computer network. Alternatively or additionally, images may be received through a hardware device (e.g. CD ROM reader; not pictured) or across a network (e.g. local area network or Internet).

In an exemplary embodiment of the invention, analytic circuitry 130 is adapted to communicate with database 110. In "on the fly" embodiments of the invention, circuitry 130 retrieves images from database 120 and constructs angle specific 2D models from the retrieved images for subsequent comparison 300 to an input image 120. In "ready to use model" embodiments of the invention, circuitry 130 retrieves existing 2D models from database 120 and compares 300 image 120 to the retrieved models. Optionally, the models can be stored in database 110 or in a data storage 140 available to analytic circuitry 130. Optionally, data storage 140 is a temporary storage buffer or cache.

In various exemplary embodiments of the invention, comparison between input image 120 and the 2D models may be conducted by software, firmware or hardware.

In an exemplary embodiment of the invention, analytic circuitry 130 and/or database 110 are installed at a central location accessible via a network from a plurality of remote locations (e.g. across the Internet). Optionally, analytic circuitry 130 of system 100 is installed at a central location and images 120 are supplied from remote locations.

Optionally, database 110 of system 100 is installed at a central location and analytic circuitry 130 addresses queries to database 110 from remote locations each time an input image 120 is provided 310.

In an exemplary embodiment of the invention, installation of circuitry 130 and/or database 110 at a central location contributes to ease of updates. Optionally, the updates become available to users at multiple remote locations and/or to follow usage by multiple user and/or contributes to a reduced computing equipment requirement at remote user locations.

In an exemplary embodiment of the invention, system 100 contributes to an increase in a level of service at a small or understaffed medical facility.

Optionally, access to database 110 and/or analytic circuitry 130 reduces a need for an experienced radiologist.

In an exemplary embodiment of the invention, a clinically useful model of a single bone from a series of angles θ comprising a single view stored in database 110 occupies 7, 10, 15, 50 or 100 MB or lesser or greater or intermediate amounts of memory. Optionally, the amount of memory occupied by database 110 varies as the number of images and/or the number of angle specific 2D models and/or an angular difference between the models.

An exemplary database 110 based upon 299 femur images and used to generate the models and perform the image analyses presented hereinbelow occupies about 10 MB of computer memory. Optionally, a larger database based upon more images can provide 2D models characterized by lower variance and/or supply a larger number of models with smaller angular differences between them.

Analytic circuitry 130 can output results of comparison and/or analysis to data storage 140 and/or display 150. Optionally, the results include a diagnosis 160 resulting from a diagnosis procedure 400.

Optionally, diagnosis procedure 400 is performed by a diagnostic module. In an exemplary embodiment of the invention, the results of diagnosis procedure 400 (diagnosis 160) are presented as markings on input image 120. The results may include, but are not limited to, one or more of a determined estimated angle of incidence, a contour, one or more anatomic features (e.g. distances, aspect ratios, angles), one or more bone parameters (e.g. trabecular direction and/or spacing and/or bone mineral density).

Optionally, diagnosis 160 includes an analysis of how the contour and/or features and/or parameters conform to normative values.

While system 100 is described as a collection of separate functional components, two or more components may be integrated into a single physical entity. Alternatively or additionally, functions described as being performed by a single component may be distributed among two or more separate physical entities. For example, although analytic circuitry 130 is depicted as a single item for clarity, it may be physically divided among various pieces of hardware, with each hardware item performing a specific function. Alternatively or additionally, although database 110 is depicted as a single item for clarity, it may be physically divided among various servers, with each server being queried by analytic circuitry 130 each time an input image 120 is provided.

In an exemplary embodiment of the invention, diagnosis 400 comprises comparing multiple input images 120 one to another 418. In an exemplary embodiment of the invention, consideration of angle of incidence θ when comparing multiple input images 120 makes diagnosis 160 resulting from diagnostic procedure 400 more accurate and/or reliable.

Database Construction

Figure 2A:
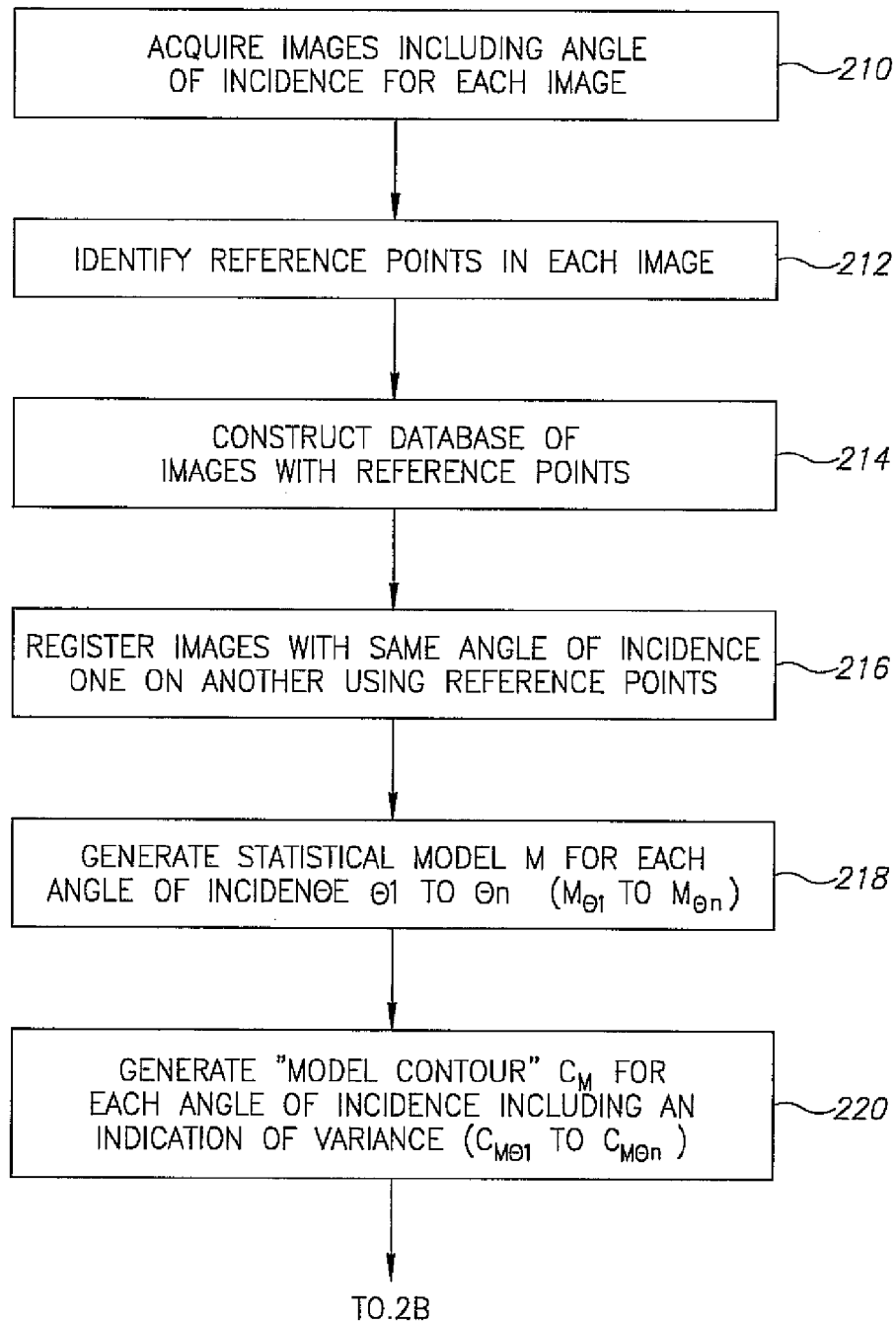
FIGS. 2A and 2B are a simplified flow diagram illustrating procedures associated with an exemplary construction method for a statistical model database used in some embodiments of the invention.
Figure 2B:
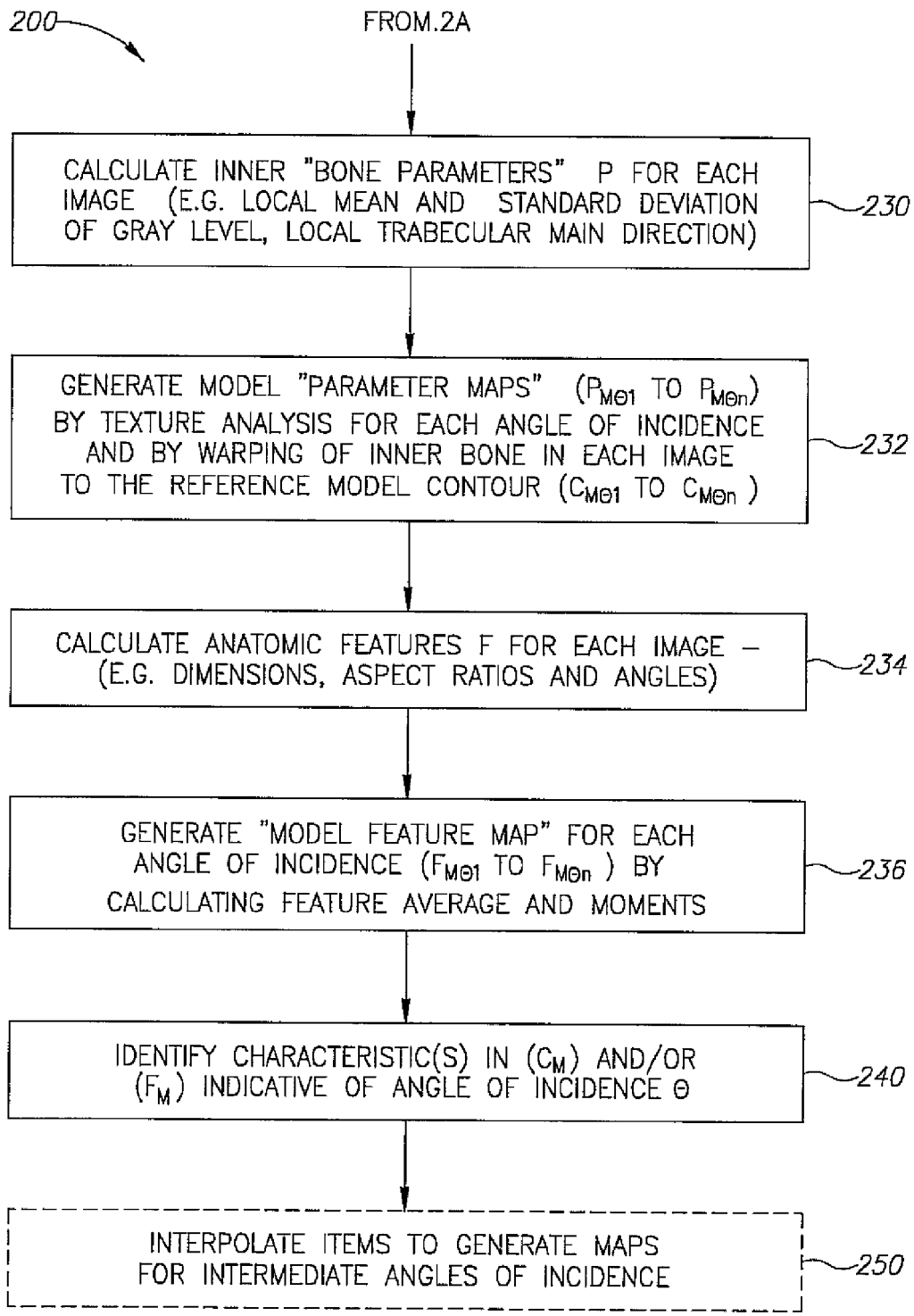

FIGS. 2A and 2B illustrate an exemplary method 200 for construction of database 110. Method 200 begins with acquisition 210 of a plurality of images of an organ, with each image being characterized by an angle of incidence θ between the imaged organ and an image capture device. While figures presented hereinbelow depict a femur, the principles described herein can be applied to other bones including but not limited to humerus, vertebrae (especially cervical vertebrae), the ankle, the shoulder, the elbow and the knee.

Alternatively or additionally, the principles described herein can be applied to joints comprising two bones. Optionally, for joints, each bone comprising the joint can be modeled separately and/or the joint may be considered in its entirety. Joint modeling is described in grater detail hereinbelow.

For any given organ (e.g. bone), a set of determinants including one or more of relevant reference points, anatomic features (F) and inner bone parameters (P) are decided upon prior to model construction. Optionally, the reference points are used to generate a contour (C). An exemplary set of femur reference points are described in greater detail hereinbelow in "Defining exemplary femur reference points".

Each image placed into database 110 is characterized with respect to this set of determinants. Registration of multiple images is performed based on reference points, optionally the contour, of each bone segment. Optionally, registration is via a warping technique. An exemplary warping method is described by Lee et al. (Lee, S. Y. et al. Image morphing using deformation techniques" (January, 1996) 7(1): 3-23, the contents of which is fully incorporated herein by reference).

In an exemplary embodiment of the invention, a statistic of each inner bone parameter (P) is calculated on a pixel by pixel basis so that distribution, mean and deviation values can be employed in modeling.

Images may be acquired either as digital images or on conventional X-ray film. If film is employed, the image can be scanned and converted to a digital image.

Optionally, the angle of incidence is determined manually during image acquisition 210, for example by measurement, or after image acquisition, for example by use of fiducial markers. Optionally, relative positions between fiducial markers in an image are indicative of angle of incidence θ. One method of ascertaining the angle of incidence of an X ray image suitable for use in the context of method 200 is disclosed in U.S. Pat. No. 6,206,566; which is fully incorporated herein by reference.

In an exemplary embodiment of the invention, images are collected from many subjects. Optionally, the subjects cover a range of ages, both genders, a variety of ethnic backgrounds and a range of physical sizes. Optionally, images may be sorted within database 110 by relevant criteria (e.g. for pelvis, gender sorting may be appropriate). In an exemplary embodiment of the invention, an influence of heterogeneity among the subjects is reduced by a scaling and/or registration process 216. In an exemplary embodiment of the invention, scaling and/or registration make the angle of incidence the primary variable.

In some embodiments of the invention, each subject contributes a single image acquired at a single angle of incidence. In other embodiments of the invention, a single subject contributes a series of images of an organ, each image acquired at a different angle of incidence. Optionally, a single 3D image (e.g. computerized tomography scan) is used to provide a series of simulated X-ray images from different angles from a single subject by projection.

In an exemplary embodiment of the invention, reference points are identified 212 in each image. Organ specific reference points are chosen based upon general characteristics of an organ so that a sufficient number of reference points can be expected to appear in substantially all images used in construction of database 110. Examples of suitable reference points include, but are not limited to, an apex, endpoints of a transverse line at a specified position (e.g. widest point or narrowest point) and a point at which a contour changes direction. Optionally, two types of reference points can be employed, anatomic landmarks and intermediate points on lines connecting landmarks.

In an exemplary embodiment of the invention, anatomic landmarks are used to indicate a corresponding position in every image. Optionally, anatomic landmarks contribute to increased registration reliability. In other exemplary embodiments of the invention, the number of available anatomic landmarks is considered insufficient. In these cases, segments can be defined on lines connecting the anatomic landmarks, for example along a contour with defined number of intermediate points. Optionally, these intermediate points can serve as additional reference points.

Considering femur modeling as an exemplary embodiment of the invention, femur specific reference points can include, but are not limited to, endpoints of a shaft cross section at a bottom edge of the image, turning points at the lesser and/or greater trochanter, turning points on both sides of the femoral neck and/or a center of the femur head.

According to various exemplary embodiments of the invention 3, 5, 7 or 10 or intermediate or greater numbers of reference points are employed. Use of a smaller number of reference points can make data entry easier and more rapid. Use of a larger number of reference points can contribute to more accurate registration 216 and/or alignment and/or scaling.

In an exemplary embodiment of the invention, marking of a contour and/or of the anatomic landmarks is done manually on images used in database construction. Optionally, manual marking constitutes identification 212 of reference points. In some exemplary embodiments of the invention, system 100 suggests a contour and/or reference points to a human operator for approval or correction. Optionally, additional references points are generated by analytic circuitry 130. In an exemplary embodiment of the invention, identified reference points are marked on the image displayed on display 150 (e.g., using an input device such as a mouse). At this point database 110 is constructed 214 by storing the images including a specific angle of incidence and marked reference points for each image. Images may be stored in database 110 in any convenient format, for example DICOM (Digital Imaging and Communications in Medicine).

In an exemplary embodiment of the invention, a contour is manually indicated on each image. Optionally, images with manually marked models are stored in database 110 so that the contours will be available for model building. In some cases manual contour designation may be more accurate than automatic or computer assisted contour designation. For example, when a portion of an organ is partially covered by another organ, visual identification of the contour by an experienced radiologist may be more reliable than a computer generated contour. Optionally, reference points marked exactly on a manually determined image contour are sticky. The term "sticky" as used here indicates that points chosen by a human operator (e.g. radiologist) are not moved by circuitry 130.

Alternatively or additionally, contours may be determined automatically. Many methods of automatic contour definition are known, for example those described by Kass et al. or those described by Long and Thoma ("Segmentation of Medical Images under Topological-Constraints" M. Kass, A. Witkin, and D. Terzopoulos. *Snakes: Active contour models*. In First International Conference on Computer Vision, pages 259-268, London, June 1987 and "Segmentation and feature extraction of cervical spine X-ray images" by Long and Thoma (Proceedings of SPIE—Volume 3661 Medical Imaging 1999: Image Processing, May 1999, pp. 1037-1046". Each of these articles is fully incorporated herein by reference. These references describe automated segmentation, edge definition and feature extraction from medical X-ray images.

In an exemplary embodiment of the invention, the contours of femur images stored in database 110 are defined with approximately 100 points divided into 5 segments defined by anatomic reference points. Marking of the contours for model construction is optionally performed manually by selecting correct points along the contour. These chosen points are further interpolated using splines and based on the reference points regeneration of points along the contour. Optionally, this process contributes to equal distribution along the contours and accurate alignment of reference points across images.

FIGS. 5A, 5B, 5C, 5D and 5E show a series of hip images extracted from a computerized tomography scan of a single subject and covering a range of −30 degrees to +30 degrees in 15 degree steps. Below each image a corresponding contour with six reference points and several informative anatomic features is represented graphically. These images and/or their corresponding graphic representations are representative of the type of data used in construction 214 of database 110.

In an exemplary embodiment of the invention, conventional 2D images are employed instead of a 3D scan and an angle of incidence is determined during image acquisition, for example using methods described in U.S. Pat. No. 6,075, 879, the disclosure of which is fully incorporated herein by reference.

In order to generate angle specific models of the organ, a plurality of images from a specific angle of incidence ($\theta$) are registered 216 to one another using the reference points. Optionally, registration includes scaling. Registration and alignment may be, for example, as described in U.S. Pat. No. 6,990,229, the disclosure of which is fully incorporated herein by reference.

Once the images from a specific angle $\theta$ are registered with respect to one another, a model (M) for each angle of incidence $\theta$, can be generated 218. Assuming that images have been acquired from angles $\theta 1$ to $\theta n$; generation of models produces a series $M_{\theta 1}$ to $M_{\theta n}$. In an exemplary embodiment of the invention, each model M is statistical model comprising a weighted average of a set of items from all images characterized by a particular angle $\theta$. Items may include, but are not limited to, contours (C), anatomic features (F)(e.g. measurements, aspect ratios or distances) and inner bone parameters (P; e.g. internal texture, bone mineral density, trabecular thickness and/or spacing and/or direction).

In an exemplary embodiment of the invention, each model M indicates a statistical variance for one or more items in the model. Modeling of different item types is now described in greater detail.

Contour Modeling

In an exemplary embodiment of the invention, generation 220 (FIG. 2A) of each model M produces a "model contour" $C_M$. The series of models $M_{\theta 1}$ to $M_{\theta n}$ includes model contours $C_{M\theta 1}$ to $C_{M\theta n}$. Optionally, each $C_M$ is characterized by a statistical variance. Optionally, the variance is determined by PCA. An exemplary model femur contour $C_{M+20}$ is shown FIG. 6B superimposed on an image with an angle of incidence $\theta$ of +20 degrees.

Parameter Modeling

In an exemplary embodiment of the invention, calculation 230 (FIG. 2B) of inner bone parameters P for each of acquired images 210 is performed. According to various embodiments of the invention, parameters P may include, but are not limited to, one or more of trabecular parameters, cortical parameters and cartilaginous parameters.

Trabecular parameters may include, but are not limited to, one or more of trabecular direction, trabecular density and trabecular aspect ratio (continuity and/or regularity).

Cortical parameters may include, but are not limited to, one or more of distribution of gray level, edge sharpness and edge curvature (continuity and/or regularity).

Cartilaginous parameters may include, but are not limited to, one or more of distribution of gray level, edge sharpness and edge curvature (continuity and/or regularity).

Several ways to calculate P are known.

In an exemplary embodiment of the invention, P is calculated using methods described by Parkinson and Fazzalari (Fractal analysis: Methodological principles for fractal analysis of trabecular bone (2000) Journal of microscopy 198(2): 134-142; the contents of which are fully incorporated herein by reference).

In an exemplary embodiment of the invention, one or more P are calculated using methods described by Geraets et al. (Regional trabecular orientation and texture analysis: the radiographic trabecular pattern of hips in patients with hip fractures and in elderly control subjects (1998) Bone, 22(2): 165173; the contents of which are fully incorporated herein by reference). Optionally parameters P are analyzed by texture analysis methods as by W. G. M. Geraets and P. F. Van der Stelt (1991; *Analysis of the radiographic trabecular pattern*, pp. 575-581; the contents of which are fully incorporated herein by reference).

In an exemplary embodiment of the invention, P is calculated using methods described by Gougherty and Henerbry (Modification of texture analysis in CT to Xray images based on: "Lacunarity analysis of spatial pattern in CT images of vertebral trabecular bone for assessing osteoporosis (2002) Medical engineering and Physics 24:129-138; the contents of which are fully incorporated herein by reference).

In an exemplary embodiment of the invention, parameter data P for each of the images is used to generate (232) model "parameter maps" $P_{M\theta 1}$ to $P_{M\theta n}$. An exemplary parameter femur map $P_{M+20}$ is shown FIG. 713. Generation 232 optionally includes texture analysis of images characterized by a same angle $\theta$ and/or warping of P data to a relevant model contour $C_{M\theta}$. In an exemplary embodiment of the invention, more than one set of maps $P_{M\theta 1}$ to $P_{M\theta n}$ may be generated, each set of maps from a subset of images. For example, in order to prepare a set of parameter maps indicative of osteoporosis, $P_{M\theta 1}$ to $P_{M\theta n}$ can be generated using only images acquired from women aged 70 or more. A second normative set of $P_{M\theta 1}$ to $P_{M\theta n}$ can be generated from women aged 25 to 40.

At this stage, images for a common angle of incidence $\theta$ are represented as model M including a contour $C_{M\theta}$ and/or a parameter map $P_{M\theta}$ which describes inner bone organization.

Feature Modeling

In an exemplary embodiment of the invention, "anatomic features" F are calculated 234 for each image using contour and/or parameter data from individual images 210. Feature data F from images characterized by a same angle $\theta$ are employed to generate 236 a feature map $F_{M\theta}$. For angles $\theta 1$ to $\theta n$, there will be n feature maps $F_{M\theta 1}$ to $F_{M\theta n}$. Anatomic features F may include, for example, dimensions, aspect ratios or angles.

For the femur, medular canal histumus width (MCHW) and medular canal trochanter width (MCTW) (nominate) are important anatomic features F for pre-operative measurements in preparation for total hip replacement. Similarly, Neck Length and the Head Radius are important anatomic features F to define when preparing a prosthetic Femur. Shaft width (SHW) and MCHW are important anatomic features F useful in prognosis of future fracture. A moment of inertia equation which considers SHW and MCHW can provide an estimation of bone strength.

Use of Soft Tissue

In some exemplary embodiments of the invention, Contour C and/or features F and/or parameters P include soft tissue. For example, in lateral cervical spine radiographs, the retropharyngeal space is a known optional radiographic marker (Harris, J. H. (1987) "The normal cervical spine" In: the radiology of acute cervical spine trauma. Ed 2. Baltimore: Williams & Wilkins p. 20; the contents of which are fully incorporated herein by reference).

An exemplary femur feature map $F_{M+20}$ is shown FIG. 8B and is superimposed on an X-Ray image with an angle of incidence $\theta$ of +20 degrees in FIG. 8A.

Advantages of Angle Specific 2D Modeling

The general process described above as method 200 reduces a large number of individual images to n angle specific 2D models, where n in the number of different angles of incidence being considered. In an exemplary embodiment of the invention, n can be 20, 15, 10, 8, 6, 4 or lesser or greater or intermediate numbers. Optionally, models M are designated in discrete steps of 5, 10, 15 or 20 degrees or lesser or greater or intermediate angular differences. Optionally, the steps are not of uniform size. Use of models M defined by discrete angles of incidence θ permits use of a relatively small number of images for construction of database 110.

A desired number of 2D angle specific models may vary from organ to organ and/or view to view (e.g. front vs. side). In general an estimated number of models is chosen as a starting point and an acceptable functional variance is selected. Analytic circuitry 130 attempts construction of models and a lowest number of models which provided the accepted variance is adopted. Typically, the number of models which provide the desired variance may be influenced by an organ, a range of angles to be considered and the degree of acceptable variance. In exemplary embodiments presented herein, 5 angle specific models with 15 degree steps covering a range of −30 to +30 degrees provide an acceptable femur model.

In practice, it is often sufficient to cover a limited range of angles θ. The range of angles θ to be covered by models M is typically influenced by one or both of the expected amount of variation in camera positioning and the expected amount of variation in rotation of a target organ within the body. For example, if an orthopedic doctor requests a "front hip X-ray", the instruction is for an angle of incidence θ of 0 degrees. In practice, the actual angle of incidence θ may typically vary between +30 degrees and −30 degrees. However, it is not expected that the actual angle of incidence θ will vary by ±90 degrees because a 90 degree shift would produce a "side view" instead of a "front view". Variation from the requested angle may be caused, for example, by operator error and/or by motion of the patient between when they are positioned and when the image is actually captured.

Angle of incidence θ can also be influenced by position of a subject, or an organ within a subject, as opposed to camera position relative to the subject. For example, each femur may be subject to rotation within the hip. This rotation may result from an orthopedic condition, or simply from positioning of a subject on an examination table. For example, a patient lying prone an their back might rotate their feet so that their toes point slightly outward. This rotation of the foot would cause a rotation of their femur which changes angle of incidence θ independent of camera position.

For these reasons, a series of angle specific 2D models of the femur might include $M_{+45}$ degrees to $M_{-45}$ degrees in 5, 10 or 15 degree steps (n=19, 10 and 7 respectively). Optionally, one of models M corresponds to 0 degrees. In an exemplary embodiment of the invention, once models $M_{\theta 1}$ to $M_{\theta n}$ have been constructed, one or more characteristics in $C_M$ or $F_M$ indicative of angle of incidence θ are identified 240. For example, a particular bump in the contour may be apparent only at angle θ of +5 to −5 degrees.

In the exemplary femur model presented here, the length of the bulge in a horizontal axis of the lesser trochanter and the shaft width ratio grows as angle of incidence θ changes from −30 to +30 degrees as depicted in FIGS. 5A to 5E. Alternatively or additionally, the head shaft angle changes monotonically across the range of angle of incidence. In an exemplary embodiment of the invention, bath of these anatomic features included in angle specific 2D models in order to amplify differences between models from different angles of incidence θ. Optionally, use of multiple anatomic features in models M contributes to a more accurate estimation of angle of incidence θ.

Optionally, one or more items in $C_M$ or $F_M$ may be interpolated 250 to produce intermediate values corresponding to intermediate angles of incidence θ. Optionally, interpolation can contribute estimation of a relatively large number of angles of incidence θ from a small number of angle specific 2D models. However, since $C_M$ or $F_M$ as a function of angle of incidence θ may not be linear, interpolation can contribute to a reduction in accuracy of an estimate of angle of incidence θ. In order to reduce introduction of unwanted inaccuracies, interpolation is optionally employed between angle specific models separated by angular differences of 10, optionally 5, optionally 2.5 degrees or lesser or intermediate values.

Defining Exemplary Femur Reference Points

FIG. 15 illustrates exemplary anatomic locations used as reference points in an anterior-posterior image of a femur used in a model according to some embodiments of the invention. In the exemplary embodiment of the invention depicted in FIG. 15, reference points are selected along contour C (black line). Optionally, reference points are employed in scaling and/or registration during model construction. In an exemplary embodiment of the invention, similar reference points in input images 120 are employed when comparing the input image to an angle specific 2D model. Optionally, prominent anatomic locations are visually identified in each image and serve as reference points. In an exemplary embodiment of the invention, prominent anatomic locations are points at which a change in contour curvature is visibly apparent. In an exemplary embodiment of the invention, relationships between these anatomic locations are defined by mathematical expressions. Optionally, the relationships may be defined with respect to identified positions within the image or with respect to one or more of other anatomic locations. In an exemplary embodiment of the invention, segments between anatomic locations are made as regular as possible. The term "regular" as used here indicates a change in curvature along the contour.

Ideally, each segment includes a similar change in curvature. Optionally, use of regular segments provides reference points distributed throughout the organ.

In the depicted exemplary embodiment of the invention, two shaft points 1501 and 1502 are placed at intersection of the shaft and a bottom edge of the image.

Optionally, three trochanter points 1504, 1505 and 1506 are easily anatomically tractable and mathematically defined as transition points of curvature along the contour.

In an exemplary embodiment of the invention, trochanter points 1504, 1505 and 1506 are assigned after the identification of the shaft.

Optionally, neck pivots 1507 and 1508 are indicated at positions where gradients point externally to a head-neck axis.

Determining an Appropriate Number of Models

In an exemplary embodiment of the invention, the number of angle specific 2D models is selected in consideration of a computational burden on analytic circuitry 130. Optionally, a required maximum variance of a selected anatomic feature that is most affected by angle of incidence θ is designated and a number of models which meet the variance requirement is constructed. For example, in a femur model, angle of incidence θ affects head offset to a great degree so that variance in the amount of head offset can be used to define maximum tolerable variance in models M.

In an exemplary embodiment of the invention, a maximum number of models that are statistically distinguishable from one another are constructed. Using the maximum number of models that are statistically distinguishable from one another contributes to estimation of angle of incidence θ with greater accuracy.

In an exemplary embodiment of the invention, a maximum number of models that are statistically distinguishable from one another is determined experimentally, optionally by an iterative process. In the iterative process, an initial series of models comprising a large number of angle specific 2D models is constructed. The models are characterized and compared with one another. Significance of difference between each pair of successive models in the series is examined. If no significant difference between any pair of successive models is found, members of that pair are joined in a model of an intermediate angle in a next iteration. In an exemplary embodiment of the invention, iterations are repeated until each pair of successive models is significantly different. Optionally, significance between models is calculated according to a global parameter which reflects the total distance of a specific contour from the average contour of its related model, e.g. sum of square differences. In an exemplary embodiment of the invention, iteration produces a series of angle specific 2D models with different angular differences between different pairs of models.

Pathology Considerations

In an exemplary embodiment of the invention, acquisition of images 210 includes acquisition of some images characterized by at least one pathology. In the case of bone images, relevant pathologies can include, but are not limited to one or more of fracture, abnormal bone mineral density (e.g. osteoporosis) and tumor foci.

In an exemplary embodiment of the invention, construction of database 110 includes identification and/or classification of pathological images and/or construction of "pathology models" $M_{path}$. Optionally, each pathology affects one or more of contour C, parameters P and features F.

Optionally, images with known angles of incidence θ are acquired and image is linked to a diagnosis (e.g. from a physician or an automated diagnostic procedure e.g. dexa for bone mineral density estimation). The diagnosis is optionally used to exclude a pathological image from a normal angle specific 2D model.

Optionally, images are acquired without a diagnosis and individual images which are more than one, optionally two, optionally 3 standard deviations (or lesser or intermediate degrees of variance) away from an angle specific 2D model generated from the acquired images are excluded from the normal angle specific 2D model and assigned to a pathology model. Analysis of individual images can be based upon one or more of C, P and F. For P and F, one or more individual discriminants can be analyzed separately and/or as a group.

When a new input image 120 is analyzed, it is optionally compared first with normal angle specific 2D models. In an exemplary embodiment of the invention, this initial comparison to normal angle specific 2D models contributes to identification 410 of discrepancies D. Identification 410 (FIG. 4) of D can contribute to a reduction in false negatives and/or provide quantitative assessment.

In an exemplary embodiment of the invention, D are then analyzed in relation to one or more $M_{path}$. Optionally, comparison to $M_{path}$ contributes to a more exact diagnosis and/or contributes to generation of an automated decision making algorithm for classification to various pathological cases. Using this type of exemplary two step process, a specific image characterized by discrepancies D in density of regional trabecula can first be excluded from a normal 2D angle specific model and then be correlated to a specific osteoporotic stage by comparison to a series of $M_{path}$.

For example, osteoporosis is typically characterized by a reduced bone mineral density (a parameter P) from it earliest stages but may not cause any significant change in bone contours C until very advanced stages. As a result, a hip X-ray from an osteoporotic individual can include a femur with a normal contour C and an abnormal parameter map $P_M$ which shows reduced trabecular density. Optionally, angle of incidence θ for an osteoporotic bone is determined first by comparison to a series of normal 2D angle specific models, and parameters P indicative of osteoporosis are then evaluated with respect to an osteoporosis pathology model.

In another example a hip X-ray from an individual recovering from a femoral fracture can include a femur with an abnormal contour C and/or one or more abnormal features F. In cases of fracture, angle of incidence θ for is determined first by comparison to a series of normal 2D angle specific models, and irregularities in C and/or F are considered indicative of fracture pathology. The same X-ray from the individual recovering from the femoral fracture may have large portions of a parameter map $P_M$ which correspond to a normal parameter map $P_M$ with the same angle of incidence θ. This situation arises because a fracture will typically disrupt inner bone parameters only in close proximity to the fracture. Optionally, definition of an edge or gap between normal portions of parameter map $P_M$ can help to define or identify the fracture.

Optionally, each acquired image 210 may be assigned to one or more pathology models $M_{path}$. For example, a single X-ray may show evidence of severe osteoporosis and a radial fracture. In this case, the same X-ray might be assigned to both a fracture pathology model and an osteoporosis pathology model. Optionally, a defined spatial portion of the image might be assigned to one pathology model (e.g. osteoporosis) and a second portion of the same image might be assigned to a different pathology model (e.g. radial fracture of femur).

Alternatively or additionally, a pathology may be scored as to severity. For example, a femur with an abnormal parameter map $P_M$ indicative of osteoporosis might be scored as mild, intermediate or severe. Optionally, scoring reflects a degree or amount of deviation from a normal model using known algorithms for analysis of P. In an exemplary embodiment of the invention, pathology models $M_{path}$ are prepared for each degree of pathologic severity.

In an exemplary embodiment of the invention, pathologies are defined by rules and used to exclude individual images from inclusion in normal angle specific 2D models and/or to make a preliminary identification of pathology in input image 120. Rules can optionally be expressed in terms of normal ranges and/or statistical variance (e.g. ±2 standard deviations or more from a normal value). Rules can include terms relating to contour C and/or one or more parameters P and/or one or more features F.

Data Base Types

Database 110 has been described above in terms of contours C, parameters P and features F. However, in some embodiments of the invention, one or two of contours C, parameters P and features F may be sufficient for construction of a model M.

For example, if angle specific models $M_{\theta i}$-$M_{\theta n}$ are being constructed primarily for diagnosis of osteoporosis, parameters P are more important, and contours C are less important.

On the other hand, if angle specific models $M_{\theta 1}$-$M_{\theta n}$ are being constructed primarily for diagnosis of fracture, contours C and/or anatomic features F are more important and parameters P are less important.

Organ Considerations

Figures presented herein relate to analysis of a femur in a hip X-ray. However, the principles set forth hereinabove and hereinbelow may be applied to other organs.

For example, operative principles described herein may be applied to analysis of lungs in chest X-rays. Models M of lungs optionally rely on contour C and/or inner parameters P. Parameters P suitable for use in a lung model include, but are not limited to average alveolar size, average alveolar density and airway dimension.

Consideration of angle of incidence θ in a chest X-ray can be important, for example, because a patient with some pathology (e.g. chest trauma) may not be able to lie in a position that permits acquisition of a regular AP (anterior-posterior) image at zero degrees. A deviation from zero degrees can cause one and/or another of the lungs to be distorted in size in a resultant X-ray image. A difference in lung size, as defined by contour C, is often considered an important clinical indicator. In an exemplary embodiment of the invention, contralateral lungs are more accurately compared to one another by estimating angle of incidence θ using a series of angle specific 2D models as described above.

With respect to bones, models M of humerus, vertebrae (e.g. cervical spine) and ankle (e.g. tibia and/or fibula and/or talus) are expected to find clinical utility in identification and/or diagnosis of, lesions (e.g. metastatic), existing fractures, fracture risks, and/or osteoporosis.

For the vertebra, there are 6 standard points commonly collected in the field of vertebral morphometry because they indicate important anatomic features of the vertebrae. Any or all of these 6 points may serve as reference points for construction of models according to exemplary embodiments of the invention.

For the humerus, reference points based upon anatomic landmarks can be assigned based on Behiels et at ("Evaluation of image features and search strategies for segmentation of bone structures in radiographs using active shape models" (2002) Medical Image Analysis 6:47-62; the contents of which are fully incorporated herein by reference).

Angle Considerations

The description and figures presented herein describe models M which consider a single angle of incidence θ between an image acquisition device (e.g. X-ray camera) and an organ (e.g. bone). In the exemplary embodiments depicted in the figures, angle θ is an angle of rotation with respect to a long axis of the femur. However, the scope of the invention is not limited to this particular type of angle of incidence. In various exemplary embodiment of the invention, angle θ comprises alternate and/or additional angles.

In an exemplary embodiment of the invention, model M considers an angle of incidence θ between the femur and an examination table as a knee is raised.

In an exemplary embodiment of the invention, model M considers an angle of incidence θ could between the femur and a midline of the body as a foot is moved away from the midline.

Optionally, angle of incidence θ represents a sum of two or more discrete angles.

In some preferred embodiments of the invention, two or more series of angle specific 2D models (e.g. an X series and a Y series or X, Y and Z series) of an organ are constructed and an input image is matched to each set separately. In other preferred embodiments of the invention, a single series of angle specific 2D models covers angular displacements of an organ in multiple planes (e.g. X and Y or X, Y and Z) of an organ are constructed and an input image is matched to each set separately. Optionally, resolution in each plane can be different.

For the femur model presented in the figures, angle θ is measured or estimated relative to a long axis of the femur. This is because the femur at the pelvis is subject primarily to changes rotation about the long axis. However, other angular considerations, for example bending of the knee, can exert an influence on an apparent shape of portions of the femur, such as the femur head. In an exemplary embodiment of the invention, a series of angle specific 2D models which consider both rotation of the femur about its long axis and a degree of bending of the knee is constructed. Optionally, consideration of 2 angles θ contributes to an increase in accuracy or reliability.

Comparison of an Image to a Series of Angle Specific 2D Models

Figure 3A:
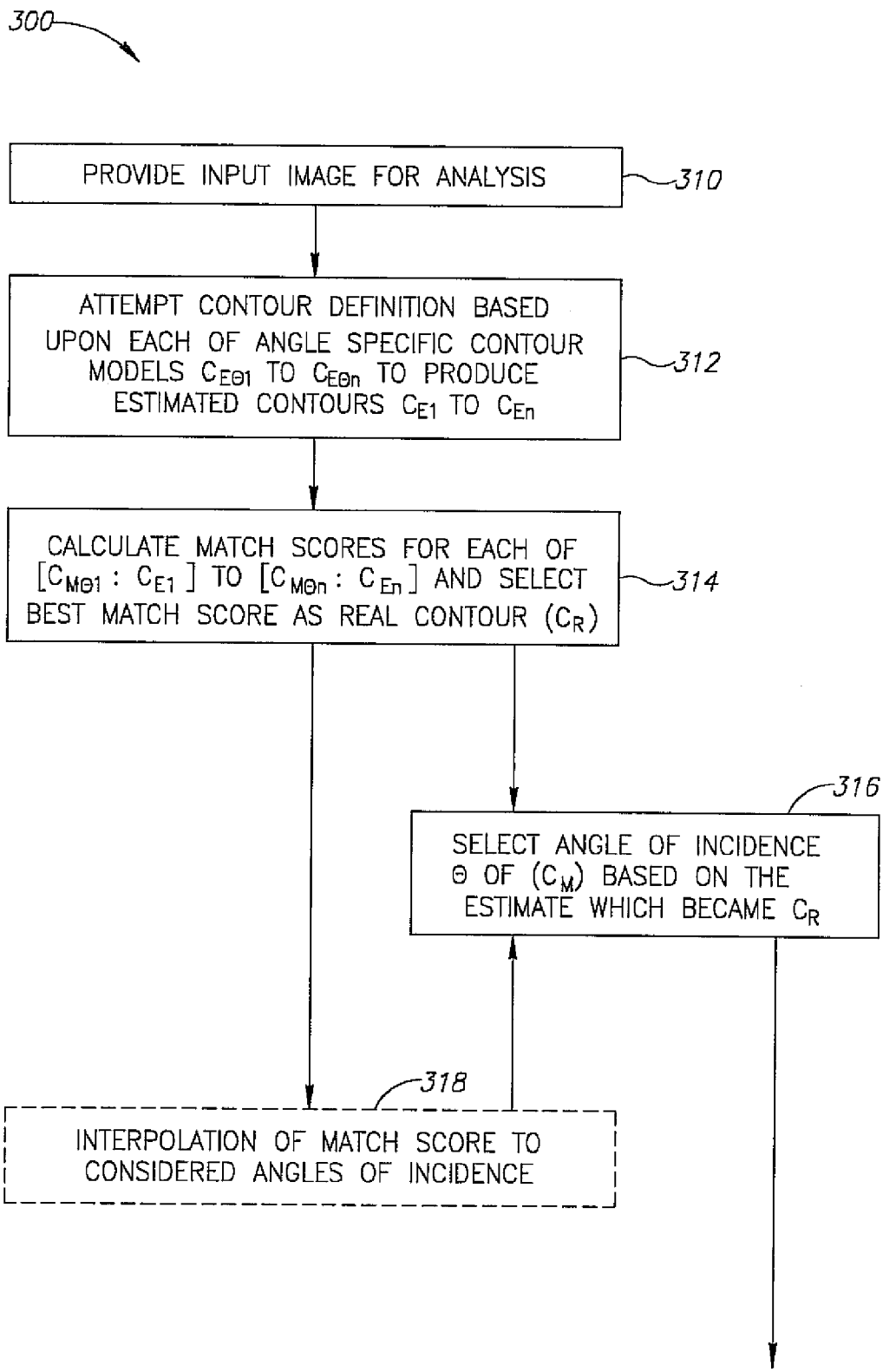
FIGS. 3A and 3B are a simplified flow diagram illustrating procedures associated with an exemplary image analysis method employing a database as described in FIGS. 2A and 2B according to some embodiments of the invention.
Figure 3B:
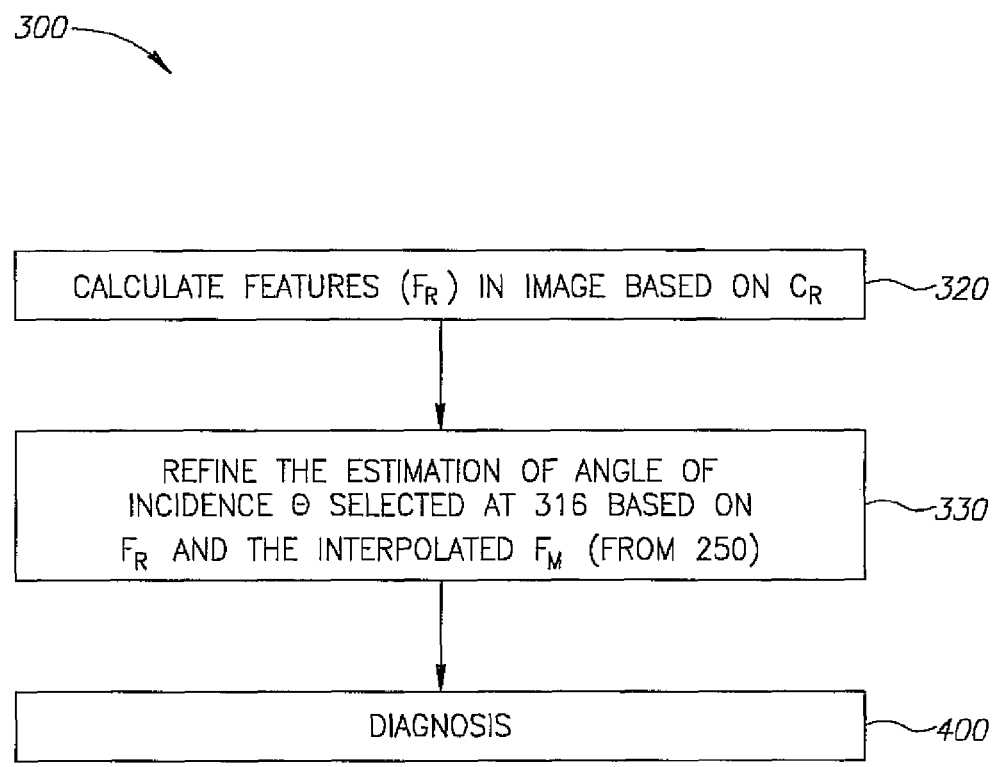

FIGS. 3A and 3B are a simplified flow diagram of an exemplary method of analysis 300 of an input image 120. Analysis 300 includes comparison to database 110 as described above.

Method 300 typically begins with provision 310 of input image 120 for analysis. Typically, input image 120 is provided 310 without exact information concerning angle of incidence θ. Optionally, image 120 may be designated front, left lateral, right lateral or rear view. In an exemplary embodiment of the invention, input image 120 is designated by organ and view (e.g. left femur; front view).

Since database 110 optionally contains many series of models M, designation of organ and/or view for image 120 contributes to matching input image 120 to a correct series of models M in database 110.

Since database 110 contains a series of models M, each model within a series for a specific angle of incidence θ, method of analysis 300 estimates an angle of incidence θ for input image 120 as it determines which model M is most relevant.

In order to estimate an angle of incidence θ for input image 120, an attempt 312 at contour definition is made by trying to fit each of $C_{M\theta1}$ to $C_{M\theta n}$ onto input image 120. This produces a series of estimated contours $C_{E1}$ to $C_{En}$. Calculation 314 of match scores for each of $[C_{M\theta}: C_{E1}]$ to $[C_{M\theta n}: C_{En}]$ is conducted and an estimated contour CE with a best match score is designated real contour ($C_R$).

Optionally, trying to fit each of $C_{M\theta1}$ to $C_{M\theta n}$ can rely on known search methods. For example, every second contour in the series can be tried first, and intermediate contours tried in regions that look promising. In other embodiments of the invention, contours are arranged in a hierarchy so meta models with variances inclusive of several angle specific 2D models are tried first, and separate angle specific 2D models within a promising meta model are tried individually afterwards.

In an exemplary embodiment of the invention, a distance map is computed from the initial attempt to match a $C_M$ to the image and the distance map is used to generate a match score. Match scores can also be generated based on other determinants. Other determinants may include, for example regional determinants such as curvature, tension and distance from an initial estimate at specific points along the contour and/or global determinants based on the entire contour such as, for example, a sum of squared distance from initial estimate and/or a sum of deformation fields calculated based on inner bone registration. These, or alternate, determinants may serve as input for more complex techniques which rely upon decision making circuitry based on one or more of regression, Bayesian decisions, trees, neural networks and k-nearest neighbor analysis. A specific implementation of contour scoring in femur segmentation is described by Chen et al. ("Automatic Extraction of Femur Contours from Hip X-Ray Images" (2005). Computer vision for biomedical image applications 3765:200-209; the contents of which are fully incorporated herein by reference).

FIGS. 12A, 12B, 12C, 12D and 12E illustrate 5 models M super imposed on an image 120. The diamond-shaped dots are the contour estimation ($C_E$). The reference contour, marked manually, is represented in the continuous line. Each final contour is graded [0-1] based on similarity to the model and the gradients in the image. The contour with the best score is the selected 316 contour (CR) which determines the estimated angle of incidence θ. In this example, model 3 of FIG. 12C is characterized by a best match score (0.99) between $C_M$ for angle θ and $C_E$. The $C_E$ of model 3 is therefore defined as real contour $C_R$. For examples presented herein, database 110 contained 299 images in total (34, 60, 122, 19 and 64 images for models 1-5 respectively). Optionally, a number of images per model increases over time.

Optionally, a match score is interpolated 318 to provide a result characterized by an angle of incidence θ between angles for which models M have been defined. In an exemplary embodiment of the invention, interpolation applies a polynomial function to at least neighboring, optionally all, available models M. Optionally, sorting of images in database 110 by patient criteria (e.g. age and/or gender) is not performed in conjunction with interpolation.

FIG. 3B illustrates that once $C_R$ is determined, real features $F_R$ can be calculated 320. Optionally, an estimation of angle of incidence θ based upon interpolation 318 of the match score, is performed. In an exemplary embodiment of the invention, $F_R$ can be used to refine 330 an estimate of angle of incidence θ.

At this stage, input image 120 is characterized by a real contour $C_R$, an angle of incidence θ and set of anatomic features $F_R$. Optionally, parameters P of input image 120 are automatically analyzed to produce a real parameter map ($P_{MR}$). At this stage, a diagnosis 400 can be performed.

Optionally, input image 120 is provided with a known angle of incidence θK. In this case an attempt 312 at contour definition is made by interpolating existing models to produce a model characterized by angle of incidence θK. $C_{θK}$ is then designated as real contour ($C_R$). If known angle of incidence θK matches one of the angles θ used to define a model M, $C_{MθK}$ is defined as $C_R$. Even if θK is known, comparison to angle specific 2D models characterized by reduced variance increases diagnostic accuracy.

Determining Discrepancies Between Input Image and Selected Angle Specific 2D Model As described above with regard to FIGS. 3A and 3B, an angle of incidence θ is estimated for each input image 120, for example, by comparison of the input image to a series of angle specific 2D models as described above with reference to FIGS. 13A through 13E.

Figure 4:
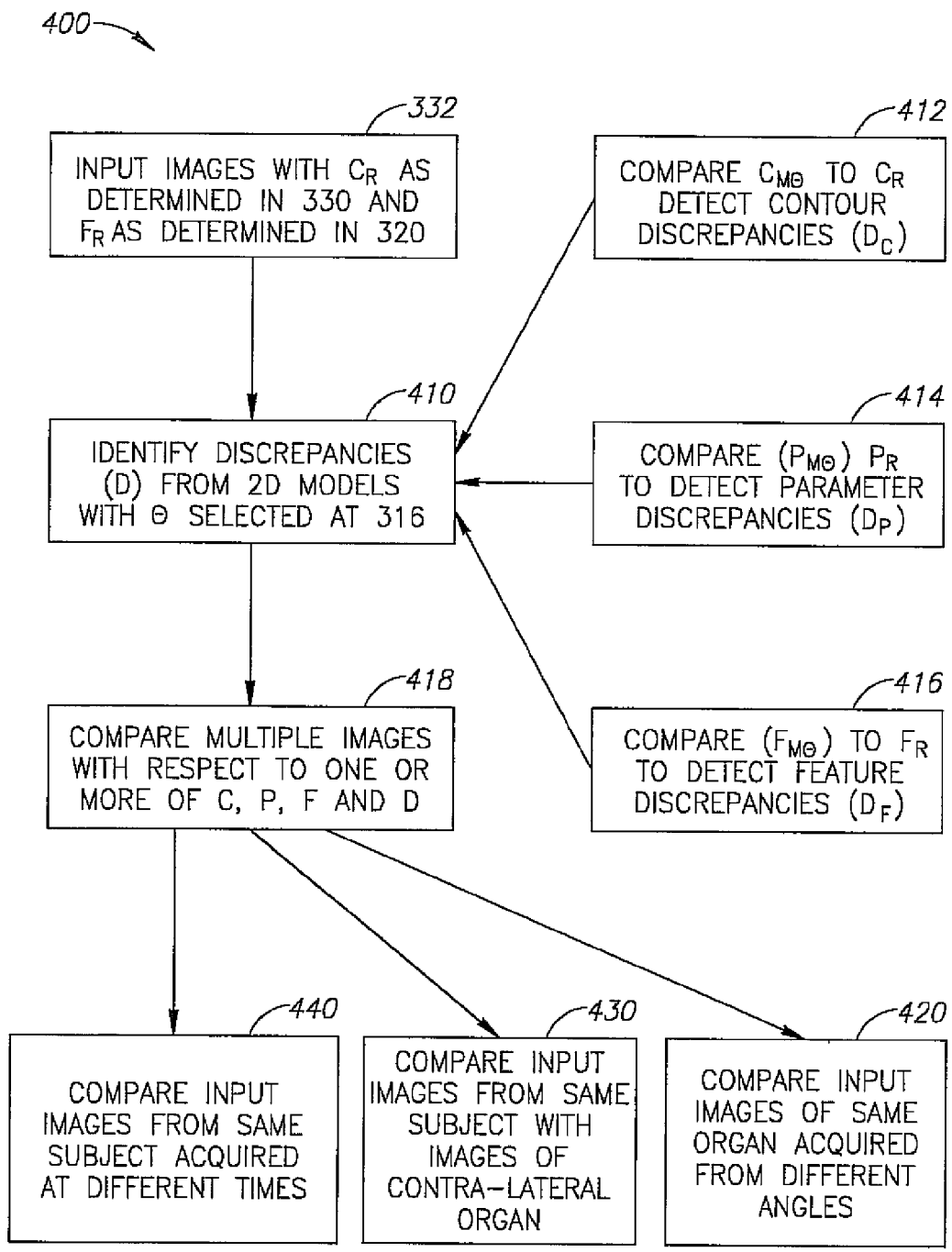
FIG. 4 is a simplified flow diagram illustrating procedures associated with exemplary medical diagnostic methods according to some embodiments of the invention.

FIG. 4 illustrates exemplary methods of diagnosis 400 which rely upon comparison of a selected angle specific 2D model and an input image which has been partially characterized.

Method 400 begins after the input image has been analyzed to the extent that it is characterized at least by an angle of incidence θ and optionally by one or more of a real contour $C_R$ and a map of real anatomic features $F_R$ as indicated at 332. Optionally, the image is further characterized by actual inner bone parameters ($P_R$), for example by texture analysis as described above.

Discrepancies D can be indicative of one or more bone pathologies and/or can monitor differences between different images acquired from a same subject. Discrepancies D between input image 120 and the 2D model representing images acquired at the same angle of incidence θ can be identified 410 in a variety of ways.

In an exemplary embodiment of the invention, comparison 412 of $C_{Mθ}$ to $C_R$ detects contour discrepancies $D_C$ between the model contour $C_{Mθ}$ and the real contour $C_R$. FIG. 6A illustrates contour discrepancies $D_C$ as grey circles. Each circle indicates a point where there is a significant difference in curvature direction and/or contour magnitude between $C_{Mθ}$ and $C_R$. In FIG. 6A $C_R$ is depicted as a series of white dots and $C_{Mθ}$ is depicted as a solid line. FIG. 6B shows $C_{Mθ}$ as a solid line superimposed on the input image. Angle of incidence θ is 20 degrees in both panels.

Discrepancies (D) are significant differences between a specific item (e.g. contour C, one or more inner bone parameters P or one or more anatomic features F) in an input image and an angle specific 2D model $M_θ$. Optionally, D considers a mean and deviation value for each item in the model. The difference (e.g. distance) between the item in the input image and a mean value of $M_θ$ is calculated and, if found to exceed 1, optionally 2, optionally 3 standard deviation units, it is considered a discrepancy D. According to various embodiments of the invention, decision making and/or matching and/or scoring of D can be by any method known in the art and/or by as CAD (computer assisted diagnosis).

Discrepancies D indicate possible abnormalities and can be of clinical diagnostic value. In an exemplary embodiment of the invention, a diagnosis considers multiple discrepancies D and a degree of deviation of each discrepancy D from an average value. According to various exemplary embodiments of the invention, various statistical methods may be employed to determine D (e.g. regression and/or Bayesian decisions and/or trees and/or neural networks and/or k-nearest neighbors). Using this approach, it is possible to calculate a variety of numerical data for each point along contour C (e.g. normal intensity gradient and/or regularity and/or continuity with respect to a length parameter).

Contour discrepancies ($D_C$) can be an indication of traumatic fractures and/or stress fractures and/or a malignant or benign lesion nearby. Parameter discrepancies ($D_P$) such as regional trabecular texture discrepancies are calculated in the segmented area by calculating the trabecular density, principal axes (orientation) and principal axes ratio. Exemplary methods for calculation of $D_P$ can be found in "Methods for comparison and detection of regional abnormalities" by Lum et al. (Combining Classifiers for Bone Fracture Detection in X-Ray Images. Proc. Int. Conf. on Image Processing, 1149-1152, 2005; the contents of which are fully incorporated herein by reference).

$D_P$ can indicate current state of bone mineral density and/or micro-architecture variations that affect bone strength. $D_P$ can also indicate a break line of displaced or un-displaced fractures and/or suggest presence of lesion.

Anatomic Features (F) such as mechanical index are optionally calculated according to geometrical measurements. The neck shaft angle (α in FIG. 8A and A in FIG. 8B) is an example of an anatomic feature in which a discrepancy $D_F$ can indicate a fracture at the proximal femur.

In another exemplary embodiment of the invention, a $D_F$ indicating narrowing along the cortical bone at the diaphysis can indicate scalloping caused by a proximal lesion.

In an exemplary embodiment of the invention, a comparison 414 of $P_{Mθ}$ to $P_R$ detects inner bone parameter discrepancies $D_P$. FIG. 7B shows $P_{Mθ}$ data superimposed on the femur head. FIG. 7A illustrates trabecular direction parameter discrepancies in a black circle relative to the same are in FIG. 7B. Angle of incidence θ is 20 degrees in both panels.

In an exemplary embodiment of the invention, a comparison 416 of $F_{Mθ}$ to $F_R$ detects anatomic feature discrepancies $D_F$. FIG. 8A illustrates anatomic features in the input image ($F_R$).

FIG. 8B shows $F_{Mθ}$ data. Angle of incidence θ is 20 degrees in both panels. Features of interest include geometrical measurements and calculations based on these measurements.

For the femur medular canal histumus width (MCHW) and medular canal trochanter width (MCTW) (nominate) are typically considered important pre-operative measures when planning a total hip replacement.

Alternatively or additionally, moment of inertia can be computed based on femur Shaft width (SHW) and femur MCHW. Moment of Inertia is an important parameter for fracture prognosis (strength estimation).

In this example, there is a difference of 15% between femur head shaft angle in the model (A of FIG. 8B) and the input image (α of FIG. 8A). Optionally, this discrepancy $D_P$ in angle α indicates an increased probability of fracture in the future. Optionally, analytic circuitry calculates interaction among two or more discrepancies D.

In an exemplary embodiment of the invention, consideration of angle of incidence θ reduces variation in measured contours (C), features (F) and parameters (P) in models M. Optionally, this contributes to a more accurate analysis of input images 120.

In FIGS. 6A, 6B, 7A, 7B, 8A and 8B, comparison 410 is between a model $M_{θ+20}$ based upon images acquired from normal individuals and an input image determined to have been acquired from the same angle. In an exemplary embodiment of the invention, comparison to one or more pathology models $M_{path}$ may be conducted in addition to or instead of comparison to a normal model.

Optionally, determination of discrepancies D between an angle specific 2D model and an input image acquired from the same angle increases sensitivity and/or early detection capability.

For example, for trabecular angle (a parameter P), construction of an angle specific 2D model reduces variance by reducing interference from differences in angle of incidence B. Reducing variance makes it easier to detect a significant discrepancy D in the trabecular angle parameter. Increased sensitivity and/or early detection may be important, for example, in identification of tumor foci and/or weakened areas which are likely to become sites of future fractures. Tumor detection and/or fracture prediction may optionally rely discriminants which are most subject to interference from changes in angle of incidence θ.

In cases where little or no difference is found between the model and the input image, system 100 optionally indicates that the input image is normal" or "healthy".

In cases where a significant discrepancy D is found between the model and the input image, system 100 optionally indicates that the input image is "abnormal". This indication may include depicting discrepancies D on the input image as shown above and/or providing a visible or audible signal and/or generation of an abnormality report. In an exemplary embodiment of the invention, an abnormality report includes a list of potential diagnoses. Optionally, a probability is assigned to each diagnosis in the report, for example, using methods described in U.S. Pat. No. 6,925,200, the disclosure of which is fully incorporated herein by reference.

In an exemplary embodiment of the invention, one or more diagnoses from the abnormality report are independently confirmed. Independent confirmation can come from comparison to non image data entered into database 110 and/or from analysis of the input image and/or non image data by a physician.

In an exemplary embodiment of the invention, after analysis of the input image is complete, the image together with its determined angle of incidence θ are added to database 110 and/or incorporated into the 2D model for angle θ. In an exemplary embodiment of the invention, if the input image includes a discrepancy D, it is added to a relevant pathology model $M_{path}$. Optionally, a substantiated diagnosis is correlated to the image in database 110 and the Image/diagnosis pair may be used in subsequent diagnoses. Methods for database update are described in, for example, Cocosco C. A. et al. (1997) BrainWeb: online interface to a 3-D MRI simulated brain database. Neuroimage 5(4):S425-27 http://citeseer.ist.psu.edu/article/cocosco97brainweb.html, the contents of which are fully incorporated herein by reference.

Presentation of Results

In FIGS. 6A, 6B, 7A, 7B, 8A and 8B, contours (C), features (F) and parameters (P) are indicated directly on images. In other exemplary embodiments of the invention, (e.g. FIGS. 5A through 5E), similar data may be presented as line drawings without superimposition on a medical image. Alternatively or additionally, data pertaining to contours (C), features (F) and parameters (P) may be presented numerically in a table or graphically (e.g. a plot of trabecular density as a function of displacement).

In cases where data is presented numerically or graphically, it may optionally be presented alongside normative values or normative ranges to make comprehension easier. In an exemplary embodiment of the invention, analytic circuitry 130 of system 100 includes a reporting module adapted to generate a report. Optionally, the report is designed to aid in diagnosis and/or prognosis and/or for planning and/or monitoring a therapeutic procedure.

Optionally, the report may describe one or more of at least one inner bone parameter (P) of a bone; at least a portion of a contour (C) of a bone and at least one anatomic feature (F) of a bone. Description is optionally numerical and/or relative to a normative value.

Optionally, the report may include one or more of a discrepancy (D) of at least one inner bone parameter (P) of a bone ($D_P$); a discrepancy (D) of at least a portion of a contour (C) of a bone ($D_C$) and a discrepancy (D) of at least one anatomic feature (F) of a bone ($D_F$).

In an exemplary embodiment of the invention, the report is employed in pre-operative planning. Optionally, the report contributes to increased probability of treatment success. Optionally, exemplary methods according to embodiments of the invention automatically extract data, and the estimated angle of incidence θ permits an accurate comparison to a normative value. This possibility is a vast improvement relative to current medical practice which typically relies upon sketches marked manually on X-ray images. Optionally, accurate and quantitative measurements find especial utility in procedures such as hip and/or knee replacement. Optionally, exemplary methods according to the invention can reduce a reliance on 3D imaging techniques such as computerized tomography.

For hip replacement, the report optionally includes one or more of head offset, head shaft angle, flare index (subtrochanteric medullar canal width divided by the medullar width at the histmus), and diameter of the femoral head.

In an exemplary embodiment of the invention, measurements provided in the report are more accurate and/or more rapidly available than comparable manual measurements. Optionally, once a single physical measurement is performed for calibration., analytic circuitry 130 calculates quantitative values for all measurements in the image.

Comparison Modes

Referring again to FIG. 4, some exemplary embodiments of the invention include comparison of multiple images 418 to determine discrepancies D in one or more of C, P and F and D.

FIGS. 9A and 9B are images of a left femur of the same subject acquired at +20 and −5 degrees respectively. According to some exemplary embodiments of the invention, concurrent comparison 420 of images of a same organ acquired at different angles to different angle specific 2D models of the organ is conducted. Optionally, use of multiple angle specific 2D models increases sensitivity of detection of discrepancies D in contour C and/or parameters P and/or features F. The head offsets indicated by arrow are 3.7 and 5.1 cm, in FIGS. 9A and 9B respectively. The head shaft angles θ are 153° and 135° in FIGS. 9A and 9B respectively. This example shows that the angle of incidence can have a dramatic effect on the image.

In an exemplary embodiment of the invention, comparison of two images acquired at different angles of incidence θ reveals abnormalities which would not have been apparent in a single image. For example, some fractures show a substantial, deformation normal to the image plane making them difficult to diagnose. In an exemplary embodiment of the invention, acquiring two images reduces a risk of missing clinically important features.

Figure 10A:
FIGS. 10A and 10B illustrate X-ray images of a right femur acquired at an angle of incidence −15 and left femur acquired at an angle of incidence +15 from the same patient respectively.
Figure 10B:
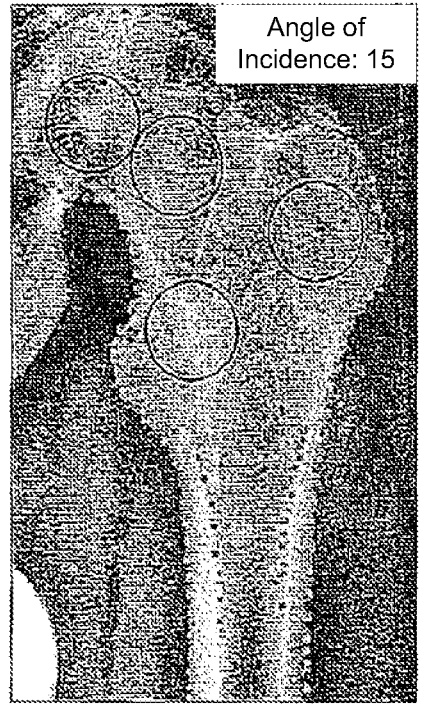

FIGS. 10A and 10B depict comparison of images of contralateral organs 430 from the same subject. FIG. 10A is an image of a right femur acquired with an angle of incidence of −15 degrees and FIG. 10B is an image of a left femur acquired with an angle of incidence +15 degrees.

As explained above, the right and left femurs may be characterized by different angles of incidence even if their images are derived from a single X-ray image. Difference in angle of incidence between contralateral organs within an image may result, for example, from anatomic abnormalities in adjacent organs (e.g., the pelvic bone in the case of a hip X-ray) and/or from slightly asymmetric positioning of the contralateral organs.

In an exemplary embodiment of the invention, a series of angle specific 2D models as described above is employed to perform an angular correction on data from one organ image so that it has a corrected angle of incidence θ which matches angle of incidence θ of the contralateral organ.

Optionally, an image of one organ is inverted or mirrored to facilitate alignment with the contralateral organ. In an exemplary embodiment of the invention, comparison of inverted aligned contralateral organs contributes to identification of differences between the organs. Optionally, the differences are clinically significant.

In another exemplary embodiment of the invention, a series of angle specific 2D models as described above is employed to perform an angular correction on data from both contralateral organs so that they share a common angle of incidence (e.g. 0 degrees).

In an exemplary embodiment of the invention the angular correction is applied to one or more features F. Optionally, an initial relative value for any specific feature F is more accurate than relative values determined by previously available modeling methods which did not consider angle of incidence θ. Optionally, comparison of a feature F from two images produces a more accurate comparison result because the values for F from each image are more accurate.

In an exemplary embodiment of the invention, each of the two images of the contralateral organs images is analyzed and compared to a most relevant angle specific 2D model. Optionally, the two images acquired from different angles of incidence θ differ in one or more of contour C, relevant features F and relevant parameters P. By analyzing each image with respect to the relevant model, it is possible to determine discrepancies $D_C$, $D_F$ and $D_P$ for each of the contralateral images. Comparison of discrepancies D between contralateral organs is optionally more informative than comparing the two images of the contralateral organs to one another. Optionally, an increase in informativity results from removing an influence of angle of incidence θ from the comparison.

Comparison of contralateral organs may be useful, for example, in confirming tumor foci or for detecting any abnormality. An initial analysis of a right femur may identify abnormalities in inner bone parameters P. These abnormalities may be tentatively identified as tumor foci. In an exemplary embodiment of the invention, comparison to parameter data P from the left femur (after appropriate angular correction) can either reveal similar abnormalities in inner bone parameters P or not. If the abnormalities in inner bone parameters P are similar in both the left and right femurs, it may suggest that the abnormalities do not represent tumor foci. If the abnormalities in inner bone parameters P are different in the left and right femurs, it may suggest that the abnormalities do represent tumor foci. Abnormalities in trabecular density (indicated by black circles) are clearly visible in the left femur. Since similar abnormalities are not present in the right femur, the asymmetric abnormalities can form the basis for a diagnosis, for example metastatic foci.

Figure 11A:
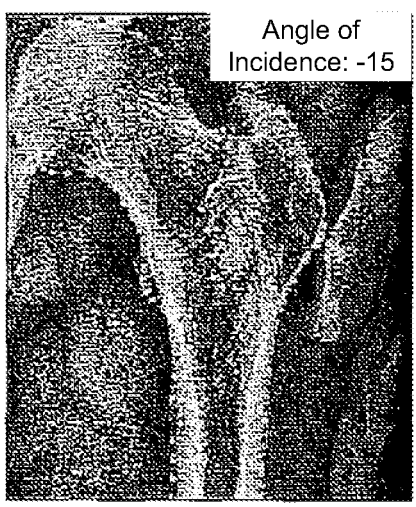
FIGS. 11A and 11B illustrate X-ray images of a left femur from a same patient taken at times 0 days and 8 days respectively and acquired at an angle of incidence −15 and 0 degrees respectively.
Figure 11B:
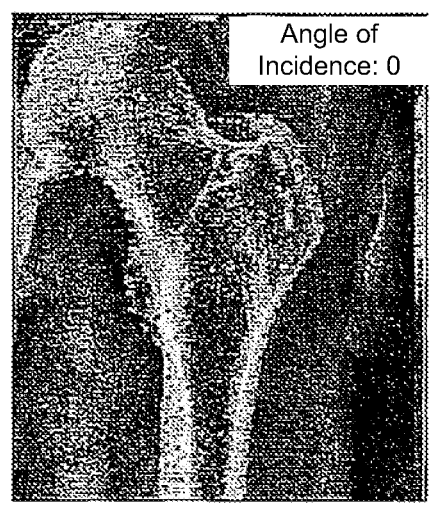

FIGS. 11A and 11B are images of a left femur from a single subject acquired at an arbitrary time 0 and 5 months later respectively. In addition, each image is characterized by a different angle of incidence θ (−15; and 0 degrees respectively). In an exemplary embodiment of the invention, comparison of input images acquired from a same subject at different times 440 can be used to track progression of clinical developments (e.g. tumor progression or fracture healing) The images are from a 70 year old subject complaining of pains in the left thigh.

Analysis of FIG. 11A according to exemplary methods described above suggested diffuse sclerosis possibly indicative of Paget's disease.

Analysis of FIG. 11B, from 5 months later, according to exemplary methods described above depicts less sclerosis and blastic lesions on proximal femoral diaphysis, and suggests osteosarcoma as a possible diagnosis.

Application of exemplary methods according to the invention contributes to formulation of a working diagnosis based upon a single X-ray image with respect to inner bone parameters (P).

In addition, these two panels illustrate the potential power of exemplary 2D angle specific models according to embodiments of the invention in making a diagnosis based on two or more images that represent a clinical progression. Optionally, the ability of methods according to the present invention to correct for variations in angle of incidence θ in temporally disparate images contributes to accuracy and/or reliability of diagnosis.

Appropriate angular corrections as described above can be applied to a temporal series of images. In an exemplary embodiment of the invention, use of appropriate angular corrections increases sensitivity of analysis of clinical progression.

Use of Non-image Data

In an exemplary embodiment of the invention, patient data is entered in conjunction with image to be analyzed 120 and/or with images acquired 210 to construct database 110. The patient data may include, for example, age, gender, ethnic heritage and/or relevant medical history. Optionally, use of non image data contributes to increased accuracy and/or reliability of analysis 300 and/or diagnosis 400. For example, comparison of an input image 120 in the form of a hip X-ray from a 3 month old infant to database 110 may yield a diagnosis 400 of "excessive cartilaginous tissue in femur". If only images in database 110 from subjects less than 6 months old are use to construct neonatal models nnM, comparison of the input image 120 from a 3 month old infant to nnM may produce a diagnosis of "normal".

In some "on the fly" exemplary embodiment of the invention, non image data associated with images in database 110 is used to select which images to employ in construction of angle specific 2D models. Examples of non image data include, but are not limited to, subject age, gender, height, weight and race.

Potential Advantages of Angle Specific 2D Models

A 2D model which is based upon images with a narrow range of angles of incidence is characterized by reduced variance in terms of contour C, parameters P and features F with respect to a similar model which does not consider angle of incidemce. Optionally, the reduction in variance increases as the range of angles for each model is reduced. The reduction in variance is seen most clearly in FIG. 13.

FIGS. 13A, 13B, 13C, 13D and 13E each depict an angle specific 2D model and its variance as determined by PCA (principle component analysis). FIG. 13F shows a model based on all 299 images (without regard to angle of incidence) employed to construct the angle specific models of the preceding 5 panels. The "general" model of FIG. 13F is characterized by a greater variance (±35 mm) than the angle specific models, especially with regard to key anatomic landmarks and/or anatomic features. For comparison, the greatest variance in an angle specific 2D model (FIG. 13C; θ=0 degrees) is ±5 mm.

FIG. 14A shows the five angle specific models of FIGS. 13A to 13E registered with respect to one another. FIG. 14B shows the 299 individual image contours used to construct the five angle specific models of FIGS. 13A to 13E registered with respect to one another.

Similarly, estimation of angle of incidence in an analyzed X-ray image may permit a more stringent automated analysis of the X-ray image. Optionally, use of a correct angle specific 2D model contributes to an increased stringency of the analysis. Optionally, more accurate scaling, registration and/or alignment of individual images used in constructing angle specific 2D models contributes to an increased stringency of analysis.

In an exemplary embodiment of the invention, an automated medical diagnosis resulting from analysis of the X-ray image by comparing to an angle specific 2D model is more accurate and/or more reliable than an automated medical diagnosis conducted using previously available technologies which do not consider the angle of incidence. Optionally, an increase in accuracy and/or reliability stems from the reduced variance in models which consider angle of incidence.

Alternatively or additionally, use of angle specific 2D models as described above reduces reliance on 3D scanning technologies (e.g. computerized tomography) by permitting estimation of an angle of incidence θ of a 2D image without performing a 3D scan on the same patient. In an exemplary embodiment of the invention, a series of angle specific 2D models constructed from images acquired from many different subjects substitutes for a CT scan acquired from a same subject that provides input image 120.

In an exemplary embodiment of the invention, the angle specific 2D models improve over time as additional images are added to database 110 from which the models are constructed. Optionally, the improvement over time will vary as the Gaussian nature of C, P and F. In some cases, the number of images in database 110 can reach a size beyond which addition of more images will not improve angle specific 2D models generated from images in database 110.

Consideration of Angle of Incidence in Modeling of Joints

In an exemplary embodiment of the invention, methods as described above are applied to analysis of joints. The term "joint" as used herein covers any junction between at least two bones. Optionally, each bone in the joint can be modeled individually using exemplary methods as described above. As a consequence, a joint model according to an exemplary model of the invention combines all states defined for each bone with respect to all states defined for every other bone in the joint. In an exemplary embodiment of the invention, joint specific features, such as articular cartilaginous dimensions and/or space dimensions between different sections of the joint are added to the model.

As described above, the angle of incidence θ of a long bone is defined by the position of two bone edges with respect to the camera. Modeling of the junction between two bones adds another edge of the second bone (first edge is constraint to the joint position). In an exemplary embodiment of the invention, this additional edge raises a number of degrees of freedom to nine Optionally, combining the two bones creates a much wider theoretical number of degrees of freedom than actually exist in the joint. In an exemplary embodiment of the invention, joint models consider changes in spatial orientation for component part of the joint. Optionally, a joint model is simplified by considering known physical constraints on range of motion of components in a particular joint in X and/or Y and/or Z directions.

FIGS. 16A, 16B, 16C, 16D, 16E and 16F are simplified schematic representations of common joint types (diarthrosis) and FIGS. 16G and 16H illustrate swing and spin movement within a joint respectively (based upon figures by Huei-Ming Chai, PhD.) While these joint types are all known, construction of angle specific 2D models which consider the relative displacement of all bones in the joint by grouping X-ray images acquired from known angles of incidence has not, apparently, been described.

FIG. 16A depicts a plane joint, also known as an irregular joint or arthrodial joint or arthrodia. Joints of this type are non-axial and are capable only of sliding movement. Plane joints are commonly found in facets of the spine. In an exemplary embodiment of the invention, a model of a plane joint considers angle of incidence θ as well as a degree of displacement between the two bones.

FIG. 16B depicts a hinged joint or ginglymus. Hinged joints are uniaxial and are characterized by a single degree of freedom. The humeroulnar joint is a uniaxial joint. In an exemplary embodiment of the invention, a model of a hinged joint considers angle of incidence θ as well as an angle of flexion, or swing, between the two bones.

FIG. 16C depicts a pivot joint, also known as a trochoid joint or screw joint. Pivot joints are uniaxial and are characterized by a single degree of freedom. The proximal radioulnar joint is a pivot joint. In an exemplary embodiment of the invention, a model of a pivot joint considers angle of incidence θ as well as a degree of rotation of one bone with respect to another bone.

FIG. 16D depicts a condyloid joint, also known as an ovoid joint or ellipsoidal joint. Condyloid joints are biaxial and are characterized by two degrees of freedom and an ovoid joint surface. The radiocarpal joint is a biaxial joint. In an exemplary embodiment of the invention, a model of a condyloid joint considers angle of incidence θ as well as a rotation of the condyloid "ball" within the chondyloid "socket". The rotation may optionally be expressed as X rotation and Y rotation or as a combined measurement reflecting the total angular displacement.

FIG. 16E depicts a saddle joint or sellar joint. Saddle joints are biaxial and are characterized by two degrees of freedom and a sellar joint surface. The first carpometacarpal joint is a biaxial joint. In an exemplary embodiment of the invention, a model of a pivot joint considers angle of incidence θ as well as a degree of rotation of each bone with respect to the other bone.

FIG. 16F depicts a ball-and-socket joint or spheroidal joint. Ball-and-socket joints are triaxial and are characterized by three degrees of freedom and a spherical joint surface. The glenohumeral joint is a ball and socket joint. In an exemplary embodiment of the invention, a model of a pivot joint considers angle of incidence θ as well as a degree of rotation of a ball portion of the joint within a socket portion of the joint. Rotation of the ball within the socket may optionally be expressed as X rotation and Y rotation or as a composite measurement reflecting the total angular displacement.

In general, osteokinematic movements in a synovial joint (between 2 bony segments) can be characterized as one of three types.

The first type is "swing" (FIG. 16G) which describes—rotary motion about a fixed axis at a proximal segment e.g. knee flexion.

The second type is "spin" (FIG. 16H) which describes axial rotation about a longitudinal axis of a distal segment e.g. forearm pronation.

The third type is "slide" (FIG. 16A) which describes linear translation of one bone with respect to another.

Exemplary Considerations for Choosing an Angular Range for Modeling Different Organs In an exemplary embodiment of the invention, a series of angle specific 2D models comprise a spatial model which describes an organ through an angular range. Optionally, the angular range is selected in consideration of a normal range of motion of the organ. Optionally, the normal range of motion may include two or more angular rotations in different planes. Optionally, only one angular rotation is deemed relevant to the model. The anatomical position is used as zero degrees unless otherwise indicated.

For example, the femur in anterior-posterior (AP) image, may exhibit all the range of rotation (e.g., −40 to +60 degrees) but only minor degree of possible flexion and tension values (same for adduction and abduction). The imaged plane is defined by the type of the image, i.e. the frontal plane.

In an exemplary embodiment of the invention, a hip model considers movement of a femur as it rotates in an acetabulum. Relevant normal ranges of motion (in degrees) for an exemplary hip model (using the anatomical position as zero degrees) are Flexion=0 to 125 degrees; Extension=0 to 30 degrees; Adduction=0 to 25 degrees; Abduction=0 to 45 degrees; External rotation=0 to 60 degrees and Internal rotation=0 to 40 degrees.

In an exemplary embodiment of the invention, a knee model considers movement of a femur with respect to the tibia and/or fibula and/or patella. Relevant normal ranges of motion (in degrees) for a Knee model are: Flexion=0 to 140 degrees and Extension–zero degrees=full extension.

In an exemplary embodiment of the invention, an ankle model considers the following ranges of motion:
(i) from that position, dorsiflexion is 0 to 20 degrees; plantar flexion is 0 to 45 degrees (neutral position is with foot at 90 degrees to leg); and
(ii) any varus or valgus angulation of the os calcis in relationship to the long axis of the tibia and fibula.

In an exemplary embodiment of the invention, shoulder, elbow, forearm, and wrist range of motion are measured with zero degrees the anatomical position with two exceptions. The first exception is that supination and pronation of the forearm are measured with the arm against the body, the elbow flexed to 90 degrees, and the forearm in mid position (zero degrees) between supination and pronation The second exception is that shoulder rotation is measured with the arm abducted to 90 degrees, the elbow flexed to 90 degrees, and the forearm reflecting the midpoint (zero degrees) between internal and external rotation of the shoulder.

In an exemplary embodiment of the invention, image analysis f an organ, depends on a position of another organ (e.g. bone) visible in a same image as a target organ. For example, upper arm bone can be analyzed after lower arm rotation and/or extension is determined.

In an exemplary shoulder model, relevant ranges of motion are: forward flexion=zero to 180 degrees; abduction=zero to 180 degrees; external rotation=zero to 90 degrees and internal rotation=zero to 90 degrees.

In an exemplary elbow model, relevant ranges of motion are: flexion=zero to 145 degrees; forearm supination=zero to 85 degrees and forearm pronation=zero to 80 degrees.

In an exemplary wrist model, relevant ranges of motion are: dorsiflexion (extension)=zero to 70 degrees; palmar flexion=zero to 80 degrees; radial deviation=zero to 20 degrees and ulnar deviation=zero to 45 degrees.

Types of Angle Specific 2D Models

Exemplary embodiments of the invention described in detail hereinabove employ contour C as a primary determinant used to estimate angle of incidence θ. However, contour based angle specific 2D models are only one of a wide variety of angle specific 2D model types.

In an exemplary embodiment of the invention, each of the angle specific 2D models includes a group of reference points on a contour (C) and the reference points serve as primary determinants.

Optionally, the reference points can be connected to define one or more of portions of contour C, optionally to define substantially all of contour (C) as in the exemplary embodiments depicted in FIGS. 13 A through 13E and 14A. In an exemplary embodiment of the invention, the angle specific 2D models rely upon at least one anatomic feature (F) as a primary determinant.

Optionally, the anatomic feature includes one or more lines connecting two reference points not along contour C. Optionally, feature F is an aspect ratio between two or more such lines.

In an exemplary embodiment of the invention, the angle specific 2D models rely upon at least one inner Parameter (P) as a primary determinant.

According to various exemplary embodiments of the invention, the angle specific 2D models can be stored and/or presented in a variety of ways.

Optionally, each of the angle specific 2D models includes a graphic representation of at least a portion of the organ. Alternatively or additionally, each of the angle specific 2D models includes a numerical representation of at least a portion of the organ in terms of one or more of C, one or more relevant P and one or more relevant F. Optionally, the numerical representations of the angle specific 2D models are provided as a lookup table.

General

The individual features described herein can be used together, in the manner above, in a single system or method. Alternatively, each of the features (or some combination or sub-combination of them) can be used separately. Specifically, features described in the practice of a method may characterize a system and features described in conjunction with a system may characterize a method. Furthermore, it should be understood that the described embodiments are exemplary in nature and are not intended to limit the scope of the invention which is defined by the claims.

The described methods and systems rely upon execution of various commands and analysis and translation of various data inputs. Any of these commands, analyses or translations may be accomplished by software, hardware or firmware according to various embodiments of the invention. In an exemplary embodiment of the invention, machine readable media contain instructions for construction of angle specific 2D models and/or comparison of input images to angle specific 2D models. In an exemplary embodiment of the invention, analytic circuitry 130 executes instructions for construction of angle specific 2D models and/or comparison of input images to angle specific 2D models.

The terms "include", "comprise" and "have" and their conjugates as used herein mean "including but not necessarily limited to".

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively or additionally, portions of the invention described/depicted as a single unit may reside in two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

All publications and/or patents and/or product descriptions cited in this document are fully incorporated herein by reference to the same extent as if each had been individually incorporated herein by reference.

The invention claimed is:

1. A medical imaging apparatus comprising:
    (a) interface circuitry adapted to receive a medical image of an organ, wherein the image was previously acquired by an imaging instrument;
    (b) image processing circuitry adapted to computationally estimate an angle of incidence between the imaging instrument and the imaged organ, based on the appearance of the imaged organ in the medical image previously acquired by the imaging instrument.

2. The apparatus according to claim 1, wherein the angle of incidence is estimated using reference points on the organ.

3. The apparatus according to claim 1, wherein the organ is a femur.

4. The apparatus according to claim 1, wherein the organ includes at least one joint.

5. An apparatus according to claim 1, wherein the medical imaging instrument is an X-ray.

6. An apparatus for estimating an angle of incidence from which a 2D medical image was captured; said apparatus comprising:
    (a) interface circuitry adapted to receive a medical image of an organ, wherein the image is acquired by an imaging instrument; and
    (b) image processing circuitry adapted to: (i) compare the received image to at least one angle specific 2D model of the organ; (ii) determine a match score between the image and the angle specific 2D model; and (iii) estimate the angle of incidence based upon the match score.

7. The apparatus according to claim 6, wherein the image processing logic is further adapted to compare at least two separate 2D medical images with one another to estimate the angle of incidence of each image.

8. The apparatus according to claim 7, wherein said image processing logic is further adapted to compare contralateral organs with one another when estimating the angle of incidence of each image.

9. A medical image analysis system comprising: (a) an input module adapted to receive an input image of an organ; (b) a digital memory including a plurality of angle specific 2D organ models, each model characterized by an angle of incidence; and (c) analytic circuitry adapted to estimate an angle of incidence of the input image by comparing the input image to at least two of the plurality of angle specific 2D organ models.

10. A system according to claim 9, wherein the input module comprises an image capture device.

11. A system according to claim 9, wherein the analytic circuitry is adapted to detect at least one discrepancy (D) between the input image and a selected angle specific 2D organ model.

12. A system according to claim 11, wherein D suggests a pathologic condition.

13. An apparatus for estimating an angle of incidence from which a radiographic image of an organ was captured; said apparatus comprising:
    interface circuitry adapted to receive the radiographic image of the organ; and
    image processing circuitry adapted to: (i) compare an appearance of the organ in the received radiographic image to at least one angle specific 2D model of the organ; (ii) determine a match score between the received radiographic image and the angle specific 2D model; and (iii) estimate the angle of incidence based upon the match score.

14. The apparatus according to claim 13, wherein the radiographic image is a fluoroscopic image.

15. The apparatus according to claim 13, wherein the radiographic image is a digital x-ray.

16. The apparatus according to claim 14, wherein the fluoroscopic image is an intra-operative image.

17. The apparatus according to claim 15, wherein the digital x-ray is an intra-operative digital x-ray.

18. The apparatus according to claim 3, further comprising second image processing circuitry adapted to detect a contour of a head of the femur.

19. The apparatus according to claim 18, wherein said second image processing circuitry is further adapted to determine parameters of the contour of the head of the femur.

20. The apparatus according to claim 13, wherein the organ is a femur and comparing an appearance of the organ in the received radiographic image to at least one angle specific 2D model of the organ includes comparing a contour of a head of the femur with a contour of the 2D model.

* * * * *